United States Patent
Masuda et al.

(10) Patent No.: US 8,598,405 B2
(45) Date of Patent: Dec. 3, 2013

(54) WASTE SOLUTION SOLIDIFYING AGENT, PROCESS FOR PREPARING THE SAME AND USE OF THE SAME

(75) Inventors: Yoshihiko Masuda, Takarazuka (JP); Masazumi Sasabe, Kakogawa (JP); Seiji Kato, Himeji (JP); Atsushi Tachibana, Himeji (JP); Kenji Kadonaga, Kakogawa (JP); Shigeru Oka, Toyonaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 430 days.

(21) Appl. No.: 11/596,068

(22) PCT Filed: May 11, 2005

(86) PCT No.: PCT/JP2005/009014
§ 371 (c)(1),
(2), (4) Date: Nov. 9, 2006

(87) PCT Pub. No.: WO2005/107940
PCT Pub. Date: Nov. 17, 2005

(65) Prior Publication Data
US 2007/0185366 A1    Aug. 9, 2007

(30) Foreign Application Priority Data
May 12, 2004   (JP) .................. 2004-142805

(51) Int. Cl.
    B09B 3/00      (2006.01)
    C02F 1/00      (2006.01)
    B01J 20/26     (2006.01)
    B01J 20/10     (2006.01)

(52) U.S. Cl.
    CPC ............... *B01J 20/103* (2013.01); *B01J 20/26* (2013.01)
    USPC ........... 604/368; 524/300; 524/322; 588/249; 588/255

(58) Field of Classification Search
    USPC ............ 524/300, 302; 604/368; 588/249, 255
    See application file for complete search history.

(56) References Cited

U.S. PATENT DOCUMENTS
4,093,776 A    6/1978   Aoki et al.
(Continued)

FOREIGN PATENT DOCUMENTS
CA    2 542 491    5/2005
(Continued)

OTHER PUBLICATIONS
Derwent Accession No. 1988-165812 which abstracts JP 63-105064.*
(Continued)

*Primary Examiner* — Ling Choi
*Assistant Examiner* — Brieann R Fink
(74) *Attorney, Agent, or Firm* — Roylance, Abrams, Berdo & Goodman, L.L.P.

(57) ABSTRACT

An object of the present invention is to provide a waste solution solidifying agent which can solidify a waste solution, particularly, a waste solution containing blood or body fluid at a low cost, uniformly, and in a short time; in particular, to provide a waste solution solidifying agent which can solidify a waste solution uniformly and in a short time in a vertically oriented waste solution equipment. As a means of achieving this object, a waste solution solidifying agent of the present invention is a particulate treating agent used in a method of treating a waste solution which solidifies a waste solution into a gel by placing a treating agent in a waste solution, and is characterized in that said agent contains, as an essential component, a water-absorbent resin having a crosslinked structure obtained by polymerizing a water-soluble ethylenic unsaturated monomer and, when flowing-placed at once into a 0.90 mass % aqueous sodium chloride solution, 20 to 95 mass % of the agent is floated, and 80 to 5 mass % is settled. And a process for preparing a waste solution solidifying agent of the present invention is a process for preparing a particulate waste solution solidifying agent containing, as an essential component, a water-absorbent resin having a crosslinked structure obtained by polymerizing a water-soluble ethylenic unsaturated monomer, and comprises a step of mixing a hydrophobic substance having a methanol index of 20 or more after polymerization.

22 Claims, 2 Drawing Sheets

(56) References Cited

U.S. PATENT DOCUMENTS

| | | | |
|---|---|---|---|
| 4,286,082 A | 8/1981 | Tsubakimoto et al. | |
| 4,367,323 A | 1/1983 | Kitamura et al. | |
| 4,446,261 A | 5/1984 | Yamasaki et al. | |
| 4,625,001 A | 11/1986 | Tsubakimoto et al. | |
| 4,683,274 A | 7/1987 | Nakamura et al. | |
| 4,732,968 A | 3/1988 | Obayashi et al. | |
| RE32,649 E | 4/1988 | Brandt et al. | |
| 4,873,299 A | 10/1989 | Nowakowsky et al. | |
| 4,973,632 A | 11/1990 | Nagasuna et al. | |
| 4,985,518 A | 1/1991 | Alexander et al. | |
| 5,051,259 A | 9/1991 | Olsen et al. | |
| 5,124,416 A | 6/1992 | Haruna et al. | |
| 5,145,906 A | 9/1992 | Chambers et al. | |
| 5,244,735 A | 9/1993 | Kimura et al. | |
| 5,250,640 A | 10/1993 | Irie et al. | |
| 5,264,495 A | 11/1993 | Irie et al. | |
| 5,380,808 A | 1/1995 | Sumiya et al. | |
| 5,866,678 A * | 2/1999 | Kajikawa et al. | 528/487 |
| 5,981,070 A | 11/1999 | Ishizaki et al. | |
| 6,071,976 A | 6/2000 | Dairoku et al. | |
| 6,228,930 B1 | 5/2001 | Dairoku et al. | |
| 6,254,990 B1 | 7/2001 | Ishizaki et al. | |
| 6,410,616 B1 * | 6/2002 | Harada et al. | 523/337 |
| 6,562,879 B1 | 5/2003 | Hatsuda et al. | |
| 8,063,265 B2 * | 11/2011 | Beck et al. | 604/368 |
| 2003/0092849 A1 * | 5/2003 | Dairoku et al. | 525/329.7 |
| 2005/0059762 A1 * | 3/2005 | Jonas et al. | 524/425 |
| 2005/0106087 A1 * | 5/2005 | Tanhehco | 423/1 |
| 2006/0282052 A1 * | 12/2006 | Saito et al. | 604/372 |

FOREIGN PATENT DOCUMENTS

| | | |
|---|---|---|
| EP | 0 559 476 | 9/1993 |
| EP | 0 686 650 | 12/1995 |
| EP | 0807646 | 11/1997 |
| EP | 0811636 | 12/1997 |
| EP | 0922717 | 6/1999 |
| EP | 0955086 | 11/1999 |
| JP | 56-133028 | 10/1981 |
| JP | 63-105064 | 5/1988 |
| JP | 6-216 | 1/1994 |
| JP | 6-248187 | 9/1994 |
| JP | 9-136966 | 5/1997 |
| JP | 9-235378 | 9/1997 |
| JP | 10-305227 | 11/1998 |
| JP | 11-106514 | 4/1999 |
| JP | 11-169451 | 6/1999 |
| JP | 11-299844 | 11/1999 |
| JP | 3224533 | 8/2001 |
| JP | 2002-35580 | 2/2002 |
| JP | 2002-119853 | 4/2002 |
| JP | 2003-020475 | 1/2003 |
| WO | WO 95/17455 | 6/1995 |
| WO | WO 95/33558 | 12/1995 |
| WO | WO 2004/069936 | 8/2004 |
| WO | WO 2004069936 A1 * | 8/2004 |
| WO | WO 2005021619 A1 * | 3/2005 |
| WO | WO 2005/042042 | 5/2005 |
| WO | WO 2005042039 A2 * | 5/2005 |
| WO | WO 2005/075070 | 8/2005 |
| WO | WO 2005111088 A1 * | 11/2005 |

OTHER PUBLICATIONS

Derwent Accession No. 1997-337115 which abstracts JP 09-136966.*

English Machine Translation of WO 2005111088 A1.*

English machine Translation of JP 2002-35580.*

Translated English equivalent of JP 63105064, 21 pages.*

* cited by examiner

Photograph of granulated water-absorbent resin K

WASTE SOLUTION SOLIDIFYING AGENT, PROCESS FOR PREPARING THE SAME AND USE OF THE SAME

TECHNICAL FIELD

The present invention relates to a particulate waste solution solidifying agent containing a water-absorbent resin, as a main component, a process for preparing the same and use of the same. More particularly, the present invention relates to a particular waste solution solidifying agent which uniformly solidifies a waste solution, in particular, a medical waste solution containing blood, body fluid or the like, and remarkably shortens a solidifying time, a process for preparing the same and use of the same.

BACKGROUND ART

In recent years, a waste solution exhausted from various industrial fields is being increased. As a waste solution, there are a factory waste solution, a beverage waste solution, and a body liquid waste solution. In particular, a liquid medical waste solution containing amniotic fluid or blood exhausted upon operation or delivery in hospitals is recovered in a waste solution canister, and is treated in a cleaning tank after burning-treatment or chemical treatment in order to prevent infectious diseases to medical workers or wasters.

However, in any case, since when a waste solution is treated in a liquid state, there is a possibility of secondary infection due to breakage of a waste solution canister or flying of a waste solution caused by occasional accidents, it is desired that a waste solution, in particular, a medical waste solution is treated after solidification (also referred to as gelling). That is, there is expected a method of treating a waste solution by placing a treating agent into a waste solution to solidify the waste solution into a gel.

Examples of a medical waste solution referred herein include blood and body fluid, a 0.90 mass % aqueous sodium chloride solution (physiological saline) mixed solution thereof, a Ringer's solution waste solution after washing of an affected part, a disinfecting ethanol waste solution, other disinfectant waste solution, an artificial dialysis waste solution, an organ containing body fluid such as blood isolated from a patient, and a pathological test waste solution.

In a waste solution treating agent for solidifying these medical waste solutions, several procedures for preventing reduction in water-absorbing performance of a water-absorbent resin due to an electrolyte contained in blood, body liquid or the like (e.g. patent documents 1 and 2 below) have been proposed. Patent document 1 describes a blend of an ionic water-absorbent resin and a nonionic water-absorbent resin. Patent document 2 describes a blend in which a substance which reduces an ionic strength of an electrolyte contained in a waste solution, for example, a chelating agent, an ion-exchange resin or ion-sensitive substance is incorporated in a water-absorbent resin.

However, in the procedure of patent document 1, although a nonionic water-absorbent resin hardly undergoes influence of an electrolyte, since an original water absorption rate is slow, in order to solidify a waste-liquid, a large amount of a solidifying time is necessary, or it is necessary to use a large amount of a water-absorbent resin. Further, a step of blending two kinds of water-absorbent resins becomes necessary, leading to a problem of non-uniform blending, or increase in a manufacturing cost.

Further, even when reduction in water-absorbing performance of a water-absorbent resin due to an electrolyte in such as patent documents 1 and 2 is prevented, there is a greater problem depending on the following waste liquid solidifying method (a shape of a canister and a method of placing a solidifying agent).

That is, as a method of solidifying a waste solution, various canister shapes (vertically oriented, laterally oriented etc.) and methods of placing a solidifying agent (simultaneous placement/divided placement into a waste liquid, pre-placement/post-placement into a solution) are proposed, but a waste solution is accommodated in a vertically oriented canister due to a problem of treating spaces in some cases.

However, when a water-absorbent resin is placed at once (post-placement in a waste solution) in order to solidify a waste solution, in particular, a medical waste solution stored in a vertically oriented waste solution canister, almost all water-absorbent resins are sunk to a canister bottom due to a density without floating, and solidification progresses towards an upper part of a waste solution. For this reason, a distribution of a water-absorbent resin after completion of solidification is such that the resin is distributed on a canister bottom at a high concentration, a part of the resin falls into a state like fisheyes in some cases, not all water-absorbent resin is used in some cases and, at an upper part of a canister, a water-absorbent resin concentration necessary for absorbing a waste solution becomes low, so the solidification is difficult to attain at an upper part of a waste solution canister.

As a result, as a method of solidifying a waste solution, when a waste solution is placed into a vertically oriented waste solution canister at once (post-placement into a waste solution), in order to solidify a whole waste solution, a large amount of a solidification time is necessary, or a large amount of a waste solution solidifying agent is necessary, in addition to a problem of non-uniform solidification between an upper part and a lower part in a vertically oriented canister.

Then, in order to shorten a time of solidifying a waste solution, a method of improving a water absorption rate by enhancing a surface area of a water-absorbent resin such as foaming and finely division of a water-absorbent resin, and a procedure of hydrophilizing a water-absorbent resin are proposed. However, under the present situation, even when a water absorption rate of a water-absorbent resin is improved, or the resin is hydrophilized, a sufficient waste solution solidifying rate is not obtained.

[Patent Document 1]
JP-A-119853/2002 (Kokai)
[Patent Document 2]
JP-A-169451/1999 (Kokai)

DISCLOSURE OF THE INVENTION

Objects of the Invention

The present invention was done in view of the aforementioned problems. The present invention is to improve the previous waste solution solidifying agent which cannot afford sufficient effect even when reduction in water-absorbing performance of a water-absorbent resin due to an electrolyte is prevented, a water absorption rate of a water-absorbent resin is improved, or a water-absorbent resin is hydrophilized, and an object of the present invention is to provide a waste solution solidifying agent which can solidify a waste solution, in particular, a medical waste solution containing blood, body fluid or the like at a low cost, uniformly and in a short time. In particular, an object of the present invention is to provide a waste solution solidifying agent which can solidify a waste solution, in particular, a medical waste solution containing blood, body fluid or the like uniformly and in a short time, in a vertically oriented waste solution canister.

SUMMARY OF THE INVENTION

The present inventors solved the aforementioned problems by finding a waste solution solidifying agent of an entirely new procedure and idea, in a waste solution solidifying agent which could not previously afford sufficient effect even when reduction in water-absorbing performance of a water-absorbent resin due to an electrolyte is prevented, a water absorption rate of a water-absorbent resin is improved, or a water-absorbent resin is hydrophilized.

That is, the present inventors found out that, in order to solidify a waste solution uniformly and in a short time, it is important that a part of a waste solution solidifying agent containing a water-absorbent resin is floated, and a remainder thereof is settled, and further also found out that, by using a substance having a certain particular hydrophobicity, a solidification time when a medical waste solution containing blood, body fluid or the like is solidified in a vertically oriented waste solution canister is remarkably shortened.

More particularly, the waste solution solidifying agent of the present invention is characterized in that a particular amount of the agent is floated, and a particular amount of the agent is settled. A true density of a water-absorbent resin depends on its monomer, and is around 1.6 g/cm$^3$ in the case of a polymer from sodium acrylate, and the polymer is not floated in a physiological saline or water (density: about 1.0 g/cm$^3$) from its true density. The present inventors found out that, by using a particular hydrophobic substance, a water-absorbent resin having a true density of about 1.6 g/cm$^3$ is floated in a physiological saline (density: about 1.0 g/cm$^3$), and a part thereof is settled.

The present invention was completed based on these findings.

That is, the waste solution solidifying agent of the present invention is a particulate treating agent used in a method of treating a waste solution by placing the treating agent into a waste solution to solidify the waste solution into a gel, and is characterized by comprising, as an essential component, a water-absorbent resin having a crosslinked structure obtained by polymerizing a water-soluble ethylenic unsaturated monomer, wherein when placed in a 0.90 mass % aqueous sodium chloride solution at once, 20 to 95 mass % of the agent is floated, and 80 to 5 mass % of the agent is settled, provided that floating and settling are defined by the state at one minute after placement of 40 g of a particulate waste solution solidifying agent at once in a measuring cylinder having an effective volume of 1000 ml (inner diameter 66 mm) which stands with a vertical axial direction and contains 1000 ml of a 0.90 mass % aqueous sodium chloride solution at 25° C.

A process for preparing a waste solution solidifying agent of the present invention is a process for preparing a particulate waste solution solidifying agent containing, as an essential component, a water-absorbent resin having a crosslinked structure obtained by polymerizing a water-soluble ethylenic unsaturated monomer, and is characterized by comprising a step of mixing a non-volatile hydrophobic substance having the following methanol index of 20 or more after polymerization. Methanol index: when 1 g of a hydrophobic substance is added to 50 ml of pure water at 25° C., in the case where this hydrophobic substance is a solid, a methanol volume (ml) at 25° C. necessary for wetting this, or in the case where this hydrophobic substance is a liquid, a methanol volume (ml) at 25° C. necessary for dispersing and/or emulsifying this.

The waste solution solidifying method of the present invention is a method of treating a waste solution by placing a treating agent into a waste solution to solidify the waste solution into a gel, and is characterized in that the waste solution solidifying agent of the present invention is used as the treating agent.

The package for solidifying a waste solution of the present invention comprises a filled waste solution solidifying agent of the present invention.

EFFECTS OF THE INVENTION

According to the present invention, upon solidification of a waste solution, a concentration of a water-absorbent resin after solidification of a waste solution becomes approximately constant regardless of a position of an upper part and a lower part of a canister, and a solidification time can be remarkably shortened. As a result, it becomes possible to reduce an amount of a waste solution solidifying agent to be used, and considerable cost down becomes possible. The waste solution solidifying agent of the present invention is obtained from a water-absorbent resin particle and a substance having a certain particular hydrophobicity.

EXPLANATION OF THE SYMBOLS

Figure 1:
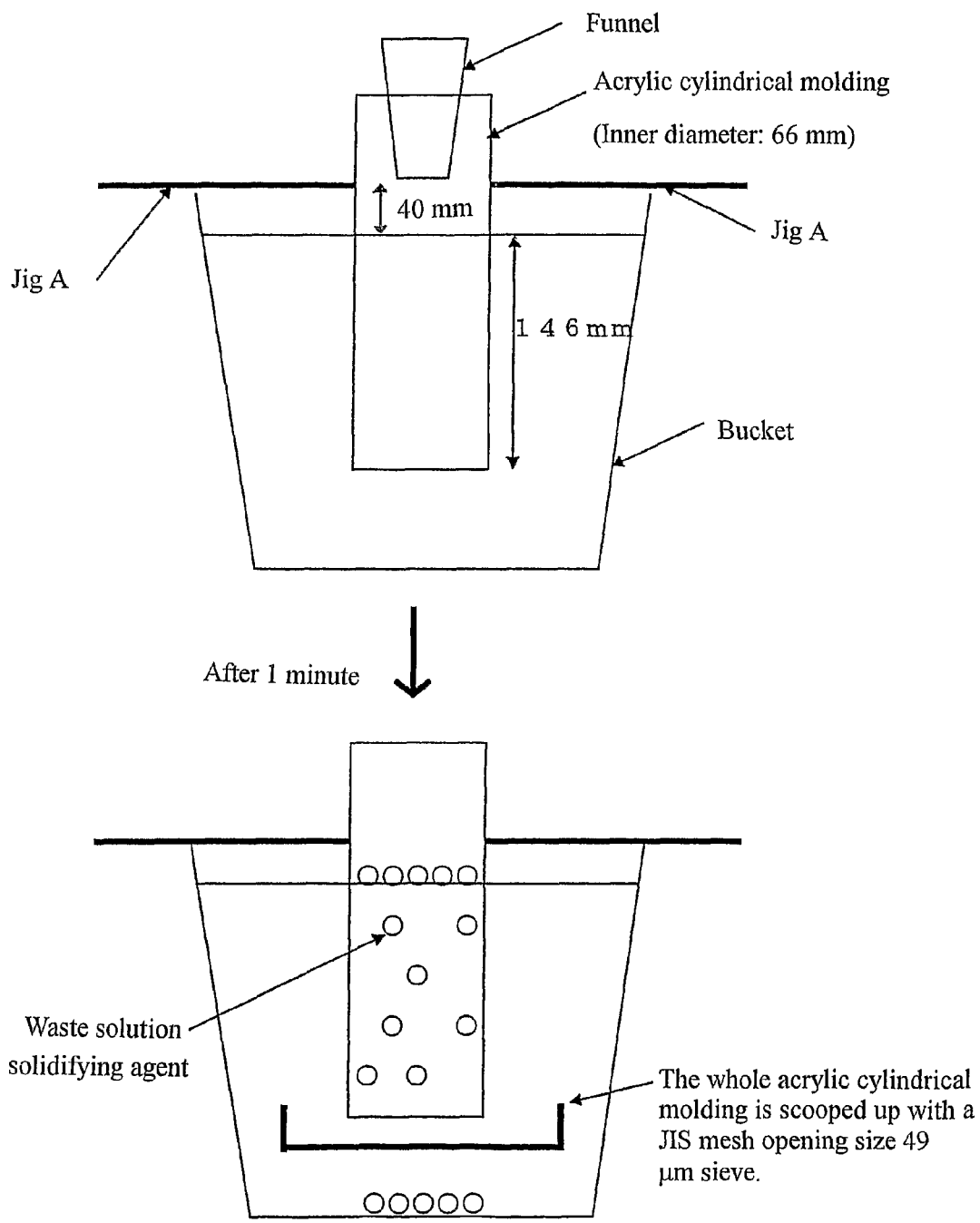
FIG. 1 is a cross-sectional view showing an outline of a construction of an apparatus for measuring a floating rate of a solidifying agent used in Examples of the present invention.

1: Funnel
2: Acrylic cylindrical molding
3: Jig A
4: Bucket
5: Waste solution solidifying agent

DETAILED DESCRIPTION OF THE INVENTION

Hereinafter, some modes for carrying out the present invention will be explained as follows, but the present invention is not limited to these.

(I) Water-Absorbent Resin

First, a water-absorbent resin of the present invention will be explained.

In the present invention, a water-absorbent resin is a water-swellable, water-insoluble and crosslinked polymer which can form a hydrogel, for example, water-swelling property refers to a resin which essentially absorbs water at a large amount of 5-folds or more, preferably 50-folds to 1000-folds of its own weight in ion-exchanged water, and water-insoluble property refers to a water-absorbent resin in which a water-extractable component content (specified in U.S. Reissue Pat. No. Re32649) in the resin is preferably 0 to 50 mass %, more preferably 0 to 25 mass %, further preferably 0 to 20 mass %, particularly preferably 0 to 15 mass %, most preferably 0 to 10 mass %. Methods of measuring them are defined in Examples.

In the present invention, as a water-absorbent resin, from a viewpoint of water absorbing property, one kind or a mixture of water-absorbent resins having a crosslinked structure obtained by polymerizing a water-soluble ethylenic unsaturated monomer is essentially used and, from a viewpoint of a water absorption rate, the resin is preferably a water-absorbent resin obtained from a water-soluble ethylenic unsaturated monomer containing an acid group, particularly a carboxyl group and, more preferably, a polyacrylic acid partially neutralized polymer obtained by polymerizing and crosslinking a monomer containing acrylic acid and/or a salt thereof (neutralized product) as a main component is better. In addition, when a water-absorbent resin obtained from a water-soluble ethylenic unsaturated monomer containing an acid group is used, in order to improve salt resistance, a nonionic water-absorbent resin such as crosslinked polyethylene oxide, and a cationic water-absorbent resin such as crosslinked polyethylenimine may be used jointly.

(1) Water-Soluble Ethylenic Unsaturated Monomer

As a water-soluble ethylenic unsaturated monomer (hereinafter, simply abbreviated as monomer), acrylic acid and/or a salt thereof is preferably used as a main component, and other monomer may be used jointly, or other monomer may be used as a main component to obtain a water-absorbent resin.

Examples of the aforementioned monomer other than acrylic acid include acid-group-containing unsaturated monomers (e.g. methacrylic acid, (anhydrous) maleic acid, fumaric acid, crotonic acid, itaconic acid, vinylsulfonic acid, 2-(meth)acrylamido-2-methylpropanesulfonic acid. (meth) acryloxyalkanesulfonic acids, and their alkaline metal salts and ammonium salts), N-vinyl-2-pyrrolidone, N-vinylacetamide, (meth)acrylamide, N-isopropyl(meth)acrylamide, 2-hydroxyethyl (meth)acrylate, methoxypolyethylene glycol (meth)acrylate, polyethylene glycol (meth)acrylate, N,N-dimethyl(meth)acrylamide, isobutylene, and lauryl (meth) acrylate. Among them, monomers which are not water-soluble (hydrophobic unsaturated monomers) may be also used as co-monomers.

When acrylic acid (salt) is used in the present invention, it is preferable that a ratio of the monomer other than acrylic acid (salt) is preferably 0 to 30 mol %, more preferably 0 to 10 mol % relative to a total amount of acrylic acid and a salt thereof as main components. When a ratio is in this range, in addition to a solidification time, other function such as antibacterial property and deodorization is imparted and, at the same time, a waste solution solidifying agent can be obtained at a further low cost.

When an acid group-containing unsaturated monomer is used as a monomer, from a viewpoint of a solidification time, at least a part thereof is preferably neutralized, as a salt thereof, there are an alkaline metal salt, an alkaline earth metal salt, and an ammonium salt. From a viewpoint of performance, easiness of industrial obtaining, and safety of the resulting water-absorbent resin, a sodium salt and a potassium salt are particularly preferable. A neutralization rate of an acid group (mol % of a neutralized acid group among a whole acid group) is preferably 10 to 100 mol %, more preferably 30 to 90 mol %, further preferably 40 to 80 mol %. In order to form the salt, an acid may be neutralized in the state of a monomer, or an unneutralized monomer and a neutralized monomer may be mixed, or an acid may be neutralized as a polymer during polymerization of a monomer or after polymerization, or they may be used jointly.

(2) Crosslinking Monomer (Inner Crosslinking Agent)

A water-absorbent resin essentially has a crosslinked structure. As the water-absorbent resin, there may be a self-crosslinking type using no crosslinking monomer, but a resin obtained by copolymerizing or reacting a crosslinking monomer (also refers to as inner crosslinking agent of water-absorbent resin) having two or more polymerizable unsaturated groups, or two or more reactive groups in one molecule is further preferable.

Inner crosslinking agents may be used alone, or two or more kinds may be appropriately used by mixing them. In addition, they may be added to a reaction system before polymerization, during polymerization or after polymerization at once or in a division manner. When at least one kind or two or more kind of inner crosslinking agents are used, taking absorbing property of a finally obtained water-absorbent resin or waste solution solidifying agent into consideration, it is preferable to essentially use a compound having two or more polymerizable unsaturated groups at polymerization.

Examples of the internal crosslinking agent include N,N'-methylenebis(meth)acrylamide, (poly)ethylene glycol di(meth)acrylate, (poly)propylene glycol di(meth)acrylate, glycerin tri(meth)acrylate, glycerin acrylate methacrylate, (ethylene oxide-modified) trimethylolpropane tri(meth)acrylate, pentaerythritol hexa(meth)acrylate, triallyl (iso)cyanurate, triallyl phosphate, triallylamine, poly(meth)acryloxyalkane, (poly)ethylene glycol diglycidyl ether, glycerol diglycidyl ether, ethylene glycol, polyethylene glycol, propylene glycol, glycerin, pentaerythritol, ethylenediamine, ethylene carbonate. propylene carbonate, polyethylenimine, and glycidyl (meth)acrylate.

From a viewpoint of physical properties, an amount of these inner crosslinking agents to be used is in a range of preferably 0.001 to 2 mol %, more preferably 0.005 to 0.5 mol %, further preferably 0.01 to 0.2 mol %, particularly preferably 0.03 to 0.15 mol % relative to the monomer (except for inner crosslinking agent).

(3) Polymerization Initiator

As an initiator which is used upon polymerization of the aforementioned monomer in order to obtain a water-absorbent resin used in the present invention, radical polymerization initiators such as potassium persulfate, ammonium persulfate, sodium persulfate, potassium peracetate, sodium peracetate, potassium percarbonate, sodium percarbonate, t-butyl hydroperoxide, hydrogen peroxide, and 2,2'-azobis(2-amidinopropane) dihydrochloride, and photopolymerization initiators such as 2-hydroxy-2-methyl-1-phenyl-propane-1-one can be used. From a physical aspect (water absorption capacity, extractable component content, remaining monomer etc.), an amount of these polymerization initiators to be used is usually 0.001 to 2 mol %, preferably 0.01 to 0.1 mol % (relative to a whole monomer).

(4) Polymerization Method

When the aforementioned monomer is polymerized in order to obtain the water-absorbent resin used in the present invention, bulk polymerization or precipitation polymerization is possible, but from a performance aspect, and from a viewpoint of easiness of control of polymerization, and absorption property of a swelling gel, it is preferable to perform aqueous solution polymerization or reverse phase suspension polymerization by using the monomer as an aqueous solution.

When a monomer is used as an aqueous solution, a concentration of a monomer in the aqueous solution (hereinafter, referred to as monomer aqueous solution) is determined by a temperature of an aqueous solution and a monomer, and is not particularly limited, and is preferably 10 to 70 mass %, more preferably 20 to 60 mass %. When the aqueous solution polymerization is performed, a solvent other than water may be used jointly if necessary, and a kind of a solvent which is used jointly is not particularly limited.

When the polymerization is initiated, it is initiated using the aforementioned (3) polymerization initiator. Alternatively, in addition to the aforementioned polymerization initiators, active energy rays such as ultraviolet rays, electron beams and γ-rays may be used alone or together with the polymerization initiator. A temperature at polymerization initiation is depends on a kind of a polymerization initiator to be used, and is preferably in a range of 15 to 130° C., more preferably in a range of 20 to 120° C. When a temperature at polymerization initiation is outside the aforementioned range, there is a possibility that a monomer remaining in the resulting water-absorbent resin is increased, or an excessive self-crosslinking reaction progresses, and water-absorbing performance of a water-absorbent resin is reduced, which is not preferable.

The reverse phase suspension polymerization is a polymerization method of suspending a monomer aqueous solution in a hydrophobic organic solvent, and is described, for example, in U.S. Pat. No. 4,093,776, U.S. Pat. No. 4,367,323, U.S. Pat. No. 4,446,261, U.S. Pat. No. 4,683,274 and U.S. Pat. No. 5,244,735. Aqueous solution polymerization is a method of polymerizing a monomer aqueous solution without using a dispersing solvent, and is described, for example in U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, and U.S. Pat. No. 5,380,808, and EP 0811636, EP 0955086, and EP 0922717. Monomers and initiators exemplified in these polymerization methods can be applied to the present invention.

(5) Drying

A water-absorbent resin obtained after the aforementioned polymerization, a substance is usually a hydrous gel-like crosslinked polymer and, if necessary, dried, and is usually pulverized before and/or after drying.

As a drying method, various methods of obtaining an objective water content such as heating drying, hot air drying, drying under reduced pressure, infrared drying, microwave drying, dehydration by azeotropy with a hydrophobic organic solvent, and high humidity drying using high temperature water steam can be adopted, and a drying method is not particularly limited to them.

When drying is performed, drying is performed in a temperature range of usually 60 to 250° C., preferably 100 to 220° C., more preferably 120 to 200° C. A drying time depends on a surface area and a water content of a polymer, and a kind of a drier, and is selected so that an objective water-content is obtained.

A water content of a water-absorbent resin (composition) which can be used in the present invention (defined as a water amount contained in a water-absorbent resin or a waste solution solidifying agent/measured by a drying reduction in amount at 180° C. for 3 hours) is not particularly limited, from a physical property aspect of the resulting waste solution solidifying agent, a resin is a powder exhibiting flowability even at a room temperature, and the resin is in the powder state of more preferably 0.2 to 30 mass %, further preferably 0.3 to 15 mass %, particularly preferably 0.5 to 10 mass %. A preferable particle diameter of a water-absorbent resin (composition) will be described later.

(6) Surface Crosslinking Treatment (Also Simply Referred to as Surface Crosslinking)

A water-absorbent resin used in a waste solution solidifying agent in the present invention may be ones obtained by the aforementioned crosslinking polymerization and drying (or partial drying) and, if necessary, pulverizing, and further surface crosslinking (secondary crosslinking) treatment.

As a crosslinking agent for performing crosslinking on the surface, there are various kinds of crosslinking agents and, from a viewpoint of physical property, generally, a polyhydric alcohol compound, an epoxy compound, a polyvalent amine compound or a condensate with its haloepoxy compound, an oxazoline compound, a mono-, di- or polyoxazolidinone compound, a polyvalent metal salt, and an alkylene carbonate compound are used. A surface crosslinking agent used in the present invention is specifically exemplified in U.S. Pat. No. 6,228,930, U.S. Pat. No. 6,071,976 and U.S. Pat. No. 6,254,990. Examples thereof are not particularly limited and include polyvalent alcohol compounds such as mono-, di- or poly-, ethylene glycol, propylene glycol, 1,3-propanediol, dipropylene glycol, 2,3,4-trimethyl-1,3-pentanediol, glycerin, 2-butene-1,4-diol, 1,4-butanediol, 1,3-butanediol, 1,5-pentanediol, 1,6-hexanediol and 1,2-cyclohexanedimethanol, epoxy compounds such as mono-, di- or poly-, ethylene glycol diglycidyl ether and glycidol, oxazolidinone compounds such as 2-oxazolidinone, and alkylene carbonate compounds such as ethylene carbonate, being not limiting. In order to maximize the effect of the present invention, among these crosslinking agents, at least polyhydric alcohol is preferably used, and a polyhydric alcohol of a carbon number of 2 to 10, more preferably a polyhydric alcohol of carbon number of 3 to 8 is used.

An amount of a surface crosslinking agent to be used is usually 0.001 to 10 mass parts, preferably 0.01 to 5 mass parts relative to 100 mass parts of a water-absorbent resin. In the present invention, it is preferable to use water in surface crosslinking. Thereupon, an amount of water to be used is in a range of 0.5 to 20 mass parts, preferably 0.5 to 10 mass parts relative to 100 mass parts of a water-absorbent resin. Alternatively, in the present invention, besides water, a hydrophilic organic solvent may be used. An amount of hydrophilic organic solvent is in a range of 0 to 10 mass parts, preferably 0 to 5 mass parts, more preferably 0 to 3 mass parts relative to a water-absorbent resin.

Further, in the present invention, among various mixing methods, a method of pre-mixing water and/or a hydrophilic organic solvent if necessary, then, spraying or adding dropwise the aqueous solution to a water-absorbent resin, followed by mixing is preferable, and a spraying method is more preferable. An average particle diameter of a liquid droplet to be sprayed is preferably 1 to 300 μm, more preferably average 2 to 200 μm.

In addition, when a water-absorbent resin is obtained by reverse phase suspension polymerization, by dispersing the aforementioned surface crosslinking agent in a hydrophobic organic solvent at a water content of a water-absorbent resin of 5 to 50 mass %, preferably 5 to 40 mass %, more preferably 5 to 30 mass % during azeotropic dehydration and/or at completion of azeotropic dehydration after completion of polymerization, a water-absorbent resin having a crosslinking-treating surface can be obtained.

A water-absorbent resin after mixing of a surface crosslinking agent is preferably heat-treated. The condition upon the heat-treatment is such that a temperature of a water-absorbent resin or a thermal medium temperature is usually 60 to 280° C., preferably 100 to 250° C., more preferably 150 to 240° C., and a heating time is preferably 1 minute to 2 hours.

(7) Granulating Step

A water-absorbent resin used in the waste solution solidifying agent of the present invention (a water-absorbent resin obtained by subjecting a surface to crosslinking treatment as described above, if necessary) is preferably adjusted to a particular particle size described later (described in a particle size of a waste solution solidifying agent described later) in order to attain an effect that, in addition to rapid and uniform waste solution solidification, reduction in water-absorbing performance and flowability at moisture absorption due to flowability and mechanical impact force at moisture absorption of the present invention is little.

Further, a particle diameter of a water-absorbent resin or a waste solution solidifying agent may be adjusted by adding and mixing an insoluble fine particle and a hydrophilic solvent, preferably water, and further granulating the mixture depending on the purpose and the necessity. By granulation, a solidification time is shortened, and floating described later is further adjusted. When granulation is performed together with the aforementioned surface crosslinking, granulation may be performed at the same time with surface crosslinking, or may be performed separately. As a binder upon granulation, water and polyhydric alcohol are preferably used.

Examples of a process for preparing an irregular-shape granulated material include (1) a process described in JP-A-106514/1999 (Kokai), that is, a process of obtaining an irregular-shape granulated material by mixing a pre-heated aqueous solution into a water-absorbent resin fine powder (150 μm) or smaller at a high speed in a short time, and drying and pulverizing this, and (2) a process of crosslinking a part near a surface of the irregular-shape granulated material obtained in the (1). Further examples include (3) a process of mixing a water-absorbent resin which has been subjected to crosslinking of a part near a surface, and an aqueous solution at room temperature and, if necessary, drying and pulverizing the mixture to adjust a particle size.

Further, when reverse phase suspension polymerization is performed, a hydrous polymerized gel dispersed at polymerization at after polymerization may be aggregated and granulated. For granulation by reverse phase aggregation, addition of an inorganic fine particle (e.g. hydrophilic silica fine particle) (U.S. Pat. No. 4,732,968) and two-stage polymerization (EP 807646) are used.

The presence or the absence of granulation can be easily confirmed by increase in a particle size before and after thereof, reduction in an amount of a fine particle, and a micrograph of the product (water-absorbent resin and waste solution solidifying agent).

(II) Hydrophobic Substance

Then, a hydrophobic substance in the present invention will be explained.

A hydrophobic substance used in a waste solution solidifying agent which is used in the present invention is a water-insoluble or water-hardly soluble substance, and is stably non-water-absorbing (non-water-swelling), and is a non-volatile hydrophobic substance having a methanol index described later of 20 or more, preferably 30 or more, more preferably 40 or more. When the methanol index is less than 20, in order that a particular amount of a waste solution solidifying agent is floated, and a particular amount of the agent is settled, since a large amount of a hydrophobic substance is necessary, liquid-absorbing performance of a waste solution solidifying agent is reduced in some cases, and a raw material cost is further increased. In addition, solubility of a hydrophobic substance in water at 26.7° C. is preferably water-insoluble or water-hardly soluble of $10^{-1}$ g/L or less, preferably $10^{-3}$ g/L or less, more preferably $10^{-4}$ g/L or less, further preferably $10^{-5}$ g/L or less. In addition, non-water-absorbing property (non-water-swelling property) means that a water absorption capacity (CRC) described later is 1 g/g or less, preferably 0.5 g/g or less.

Methanol Index: when 1 g of a hydrophobic substance is added to 50 ml of pure water at 25° C., in the case where this hydrophobic substance is a solid, a volume (ml) of methanol at 25° C. necessary for wetting this, or in the case where this hydrophobic substance is a liquid, a volume (ml) of methanol at 25° C. necessary for dispersing and/or emulsifying this.

A hydrophobic substance is a substance containing a hydrophobic group in a molecule and, as a hydrophobic group, a chain hydrocarbon and an aromatic hydrocarbon are mainly used and, as a hydrocarbon chain grows longer, hydrophobicity is increased. Besides this, a halogenated alkyl group (RX—), an organosilicon group (e.g.: RSi $(CH_3)_2$—), and a fluorinated carbon chain (e.g.: $C_nF_{2n+1}$) belong to this.

When a hydrophobic substance is a powder, a particle diameter of a hydrophobic substance is not particularly limited, but is usually smaller than a weight (mass) average particle diameter of a water-absorbent resin, 90 to 100 mass % of a powder is 200 μm or smaller, and preferably 100 μm or smaller, more preferably 50 μm or smaller, particularly preferably 10 μm or smaller is used. A method of adding the hydrophobic substance and an amount of the substance to be added will be later described in the section hereof headed "(III) Process for preparing a waste solution solidifying agent". A lower limit of a particle diameter is usually around 0.001 μm.

It is necessary that these hydrophobic substances remain in or immobilized on a water-absorbent resin and, therefore, a substance which is solid or non-volatile at room temperature (25° C.) and a normal pressure is used. Herein, non-volatile is a substance having a boiling point at a normal pressure of essentially 150° C. or higher, preferably 200° C. or higher, more preferably 250° C. or higher, particularly preferably 300° C. or higher. Preferably, a solid is used, and a melting point thereof is 25° C. or higher, preferably 50° C. or higher, more preferably 75° C. or higher, particularly preferably 100° C. or higher. When a volatile substance is used, it becomes difficult to immobilize on a water-absorbent resin, and a problem of a smell is caused in some cases.

Examples of the hydrophobic substance include hydrocarbon, fatty acid, fatty acid ester, fatty acid amide, metal soap, silicone-based compound, surfactant, and thermoplastic resin.

(Hydrocarbon)

A hydrocarbon is not particularly limited as far as a methanol index is 20 or more, but for example, low-molecular weight polyethylene (e.g. molecular weight around 1,500 to 2,000) can be used. A methanol index of fine powder polyethylene (FLO-THENE F-1.5) manufactured by Sumitomo Seika Chemicals Co., Ltd. is 200 or more.

(Fatty Acid, Fatty Acid Amide, Fatty Acid Ester)

Fatty acid, fatty acid amide and fatty acid ester are not particularly limited as far as a methanol index is 20 or more, but fatty acid having a carbon number of 12 (C12) or more, and fatty acid amide and fatty acid ester comprising fatty acid having a carbon number of 12 (C12) or more are preferable.

Examples of fatty acid include lauric acid, myristic acid, palmitic acid, oleic acid, stearic acid, arachidic acid and behenic acid. A methanol index of stearic acid (manufactured by Wako Pure Chemical Industries, Co., Ltd.) is 100. In this respect, upon measurement of the methanol index, a substance as stearic acid was ground with a mortar, and passed through a JIS 200 μm sieve to obtain a powder, which was used.

Examples of fatty acid amide specifically include stearylamide, paltimylamide, oleylamide, methylenebisstearoamide, ethylenebisstearoamide, and erucic acid amide. A methanol index of erucic acid amide (manufactured by Tokyo Kasei Kogyo Co., Ltd.) is 150. In this respect, upon measurement of the methanol index, a substance as erucic acid amide was ground with a mortar, and passed through a JIS 200 μm sieve to obtain a powder, which was used.

Examples of fatty acid ester include stearyl stearate, methyl stearate, hardened castor oil, and ethylene glycol monostearate. A methanol index of stearyl stearate (trade name; Unister M-9676 manufactured by Nippon Oil & Fats Co., Ltd.) is 150. In this respect, upon measurement of the methanol index, a substance as stearyl stearate was ground with a mortar, and passed through a JIS 200 μm sieve to obtain a powder, which was used.

(Metal Soap)

A metal soap comprises a metal salt other than an alkaline metal salt of fatty acid, petroleum acid, polymer acid and the like which are organic acid. A metal soap is not particularly limited as far as a metal index is 20 or more. This metal soap also has an action as a stabilizer.

Examples of organic acid constituting a metal soap include long chain or branched fatty acid such as caproic acid, octylic acid, decanoic acid, lauric acid, myristic acid, palmitic acid, oleic acid, and stearic acid, petroleum acid such as benzoic acid, myristicic acid, naphthenic acid, naphthoic acid, naphthoxyacetic acid, and polymer acid such as poly(meth)acrylic acid and polysulfonic acid, and organic acid having a carboxyl group in a molecule is preferable, and more preferable examples include fatty acid such as caproic acid, octylic acid, decanoic acid, lauric acid, myristic acid, palmitic acid, oleic acid, stearic acid, tallow acid, and castor hardened fatty acid. Further preferable examples include fatty acid having no unsaturated bond in a molecule such as caproic acid, octylic acid, decanoic acid, lauric acid, myristic acid, palmitic acid, and stearic acid. Most preferable examples include long chain fatty acid of a carbon number of 12 or more having no unsaturated bond in a molecule, such as lauric acid, myristic acid, palmitic acid and stearic acid. Even when fatty acid having an unsaturated bond in a molecule is used, the object of the present invention can be attained, but there is a possibility that a waste solution solidifying agent using them produces coloring, a smell or the like when undergoes heat or oxidation during storage. As the organic acid, organic acid having a carbon number of 7 or more in a molecule is preferably used. When organic acid having a carbon number of less than 7 in a molecule is used, solubility of the hydrophobic substance in water is increased, and there is a possibility that the substance is dissolved in a medical waste solution containing blood, body fluid or the like, which is not preferable. In addition, when organic acid having a carbon number of less than 7 in a molecule such as oxalic acid and citric acid is used, since a hardness of these metal salts is high, there is a possibility that liquid absorbing property is reduced, for example, when a mechanical impact force is given. A metal salt constituting the aforementioned metal soap is not particularly limited as far as it is a metal salt other than an alkaline metal salt such as an alkaline earth metal salt and a transition metal salt, and examples thereof include a magnesium salt, a calcium salt, a strontium salt, a barium salt, a zinc salt, a cadmium salt, an aluminum salt, a tin salt, and a lead salt. Inter alia, from a viewpoint of easy availability, a barium salt, a calcium salt, a magnesium salt, an aluminum salt, and a zinc salt are preferable. In addition, a combination of the organic acid and the metal salt constituting a metal soap is not particularly limited, but they may be used alone and/or two or more kinds may be used jointly. When polymer acid such as polyacrylic acid is used as organic acid, it is preferable that 95 mol % or more, more preferably 98 mol % or more, further preferably 99 mol % or more of a carboxyl group possessed by the polymer acid forms a salt with the polyvalent metal. A molecular weight of polymer acid to be used is, in terms of a weight average molecular weight, usually 10,000 or larger, preferably 50,000 or larger. In addition, a methanol index of aluminum tristearate (deer first grade, manufactured by Kanto Kagaku, Co., Ltd.) is 150, and a methanol index of zinc stearate (deer first grade, manufactured by Kanto Kagaku, Co., Ltd.) is 200 or more.

(Silicone-Based Compound)

Examples of a silicone-based compound include hydrophobic silicon dioxide compounds in which a silicone compound (hexamethylenesilazane, monomethyltrichlorosilazane, dimethyldichlorosilane, silicone oil etc.) is added to a silanol group (Si—OH) of hydrophilic silicon dioxide, but is not particularly limited as far as a methanol index is 20 or more. In addition, a methanol index of hydrophobic silicon dioxide (trade name; Aerosil 8972; manufactured by Nippon Aerosil Co., Ltd.) is 47.

(Surfactant)

A surfactant is a substance having a hydrophilic atomic group and an oleophilic atomic group at the same time. As a hydrophilic atomic group, there are ionic moieties such as —$COO^-$, —$OSO_3^-$ and the like, nonionic moieties such as a polyoxyethylene chain and the like. As an oleophilic atomic group, there are straight or cyclic compounds such as an alkyl group, an alkylallyl group and the like. In addition, as an atomic group having both hydrophobicity and oleophobicity, there are fluorine-containing compounds such as a perfluoroalkyl group and the like. When a surfactant is seen from a viewpoint of a structure, there are ionic surfactants which are dissociated into ions, and nonionic surfactants which are not dissociated into ions. An ionic surfactant can be classified into an anionic surfactant, a cationic surfactant, and an amphoteric surfactant depending on a kind of a charge when dissociated in the aqueous solution state. A surfactant which can be used in the present invention is not particularly limited as far as a methanol index is 20 or more. Incidentally, examples of the fluorine-containing surfactants include trade name: DS-403, perfluoroalkylethylene oxide addition product, manufactured by Daikin Industries, Co., Ltd., as a nonionic one; and trade name: Ftergent 300; manufactured by Neos Co., Ltd., as a cationic one. Incidentally, the methanol index of the Ftergent 300 (cationic surfactant containing quaternary ammonium salts) is 80.

(Thermoplastic Resin)

A thermoplastic resin which can be used in the present invention has hydrophilicity and hydrophobicity, and has a weight average molecular weight of 10,000 to 1,000,000, preferably 20,000 to 500,000, more preferably 40,000 to 200,000. Herein, hydrophilicity means that a structure having a hydrophilic group such as a carboxylic acid group, a hydroxy group, an amino group, an amide group, a sulfonic acid group, a phosphoric acid group, an alkylene glycol group, and a N-methoxyamino group is possessed, and hydrophobicity means that a structure having a hydrophobic group such as an alkyl group such as a methyl group, an ethyl group, a propyl group, and a butyl group, a phenyl group, and an acetyl group is possessed.

As the thermoplastic resin, a thermoplastic resin having solubility in alcohol and insolubility in water is preferable. This is preferable for maintaining liquid permeability and promoting gelling of a whole since, by using a small amount of a thermoplastic resin having an appropriate degree of hydrophobicity and an appropriate degree of hydrophilicity, a water absorption rate is not suppressed by excessive water repellency due to a hydrophobic group and, also when contacted with an aqueous solution, a resin is not dissolved in the aqueous solution, and a viscosity of a contact solution (waste solution) is not increased. Examples of the thermoplastic resin include a copolymer of a hydrophilic monomer and a hydrophobic acryl ester monomer, polyvinyl alcohol having a low gelling degree, an alkaline water-soluble resin, hydrophobic polyvinyl alcohol, alkali-soluble nylon, and alcohol-soluble nylon. Only one kind of them may be used, or two or more kinds of them may be used jointly. Preferable is at least one kind selected from alkaline water-soluble resin, hydrophobic polyvinyl alcohol, and alkali-soluble nylon. Particularly preferable is an alkaline water-soluble resin which is alcohol-soluble and water-insoluble.

An alkaline water-soluble resin is a resin which is insoluble in water at a normal temperature and a normal pressure, but is soluble in alkaline water which was made alkaline by dissolving sodium hydroxide in ion-exchanged water at a ratio of 0.4 mass %.

As the alkaline water-soluble resin, an alkaline water-soluble resin described in Japanese Patent No. 3224533 can be used. An alkaline water-soluble resin means a resin which is not soluble in water exhibiting acidic property or neutral property, and is soluble in water exhibiting alkaline property. Herein, water exhibiting neutral property is water having a pH value in a range of 6 to 8, water exhibiting acidic property is water having a pH of less than the aforementioned neutral property range, and water exhibiting alkaline property is water having a pH value greater than the aforementioned neutral property range.

An alkaline water-soluble resin is such that a reduction rate obtained by the following assessment test as a degree of solubility in alkaline water is preferably 50 to 100%, more preferably 60 to 100%, further preferably 70 to 100%.

(Assessment Test of Solubility in Alkaline Water)

A resin is molded into a cylindrical pellet shape having a diameter of 5 mm and a length of 5 mm using a biaxial extruder, and the solubility is measured using the resultant molding. 10 g of this molding is placed into 500 g of an aqueous sodium hydroxide solution having a concentration of 0.4 mass % in 1 L of a beaker, and this is stirred at 25° C. and 300 rpm for 24 hours using four wings having a diameter of 40 mm (this is referred to as solubility test). Thereafter, a mass of the molding dissolved in alkaline water is assessed by a reduction rate from an original molding. That is, a resin matter which remains unsolved after a solubility test (after 24 hours stirring) is filtered, and washed with water, a mass after drying is obtained, and assessment is performed by obtaining a reduction rate from a mass of an original resin before a solubility test.

Reduction rate (%)=(mass (g) before solubility test–mass (g) after solubility test)/mass (g) before solubility test.

Examples of an alkaline water-soluble resin include one or two or more kinds of a resin having a substituent such as a carboxylic acid group, a sulfonic acid group, and a phosphonic acid group, a novolac resin containing a phenolic hydroxyl group, and a polyvinylphenol resin. Inter alia, a resin obtained by copolymerizing an α,β-unsaturated carboxylic acid-based monomer and a vinyl-based monomer other than an α,β-unsaturated carboxylic acid-based monomer is preferable in that it is excellent in solubility in alkaline water, economical property, and various physical properties of a resin composition. Alternatively, a cellulose-based derivative which is a resin having a carboxylic acid group such as hydroxypropylmethyl cellulose phthalate, hydroxypropylmethyl cellulose acetate succinate, cellulose acetate hexahydrophthalate, hydroxypropylmethyl cellulose acetate phthalate, and hydroxypropylmethyl cellulose hexahydrophthalate can be also used.

Examples of an α,β-unsaturated carboxylic acid-based monomer include α,β-unsaturated carboxylic acid such as acrylic acid, and methacrylic acid, α,β-unsaturated dicarboxylic acid such as itaconic acid, maleic acid, and fumaric acid, α,β-unsaturated dicarboxylic anhydride such as maleic anhydride, and itaconic anhydride, and α,β-unsaturated dicarboxylic acid monoester such as maleic acid monoester, fumaric acid monoester, and itaconic acid monoester, being not limiting. Inter alia, acrylic acid and methacrylic acid are particularly preferable in order to sufficiently exert the effect of the present invention. These α,β-unsaturated carboxylic acid-based monomers may be used alone, or two or more kinds may be used jointly.

Examples of a vinyl-based monomer include esters of monohydric alcohol of a carbon number of 1 to 18 and (meth)acrylic acid such as methyl acrylate, ethyl acrylate, propyl acrylate, butyl acrylate, stearyl acrylate, methyl methacrylate, ethyl methacrylate, propyl methacrylate, butyl methacrylate, and stearyl methacrylate, nitrile group-containing vinyl-based monomers such as acrylonitrile, and methacrylonitrile, hydroxy group-containing vinyl-based monomers such as hydroxyethyl acrylate, and hydroxypropyl methacrylate, aromatic vinyl-based monomers such as styrene, and α-methylstyrene, aliphatic vinyl-based monomers such as vinyl acetate, allyl ethers, maleic acid derivatives such as maleic acid monoalkyl ester, and maleic acid dialkyl ester, fumaric acid derivatives such as fumaric acid monoalkyl ester, and fumaric acid dialkyl ester, maleimide derivatives such as maleimide, N-methylmaleimide, N-stearylmaleimide, N-phenylmaleimide, and N-cyclohexylmaleimide, itaconic acid derivatives such as itaconic acid monoalkyl ester, itaconic acid dialkyl ester, itaconamides, itaconimides, and itaconamide esters, alkenes such as ethylene, and propylene, dienes such as butadiene, and isoprene, being not limiting. Inter alia, (meth)acrylic acid ester is particularly preferable in order to sufficiently exert the effect of the present invention.

These vinyl-based monomers may be used alone, or two or more kinds may be used jointly.

A ratio of an α,β-unsaturated carboxylic acid-based monomer accounting for a total amount of an α,β-unsaturated carboxylic acid-based monomer and a vinyl-based monomer is preferably 9 mass % or more, more preferably in a range of 9 to 40 mass %. By a ratio of an α,β-unsaturated carboxylic acid-based monomer of 9 mass % or more, the effect of the present invention can be sufficiently manifested.

A copolymerization method of obtaining an alkaline water-soluble resin by copolymerizing an α,β-unsaturated carboxylic acid-based monomer and a vinyl-based monomer, that is, a process for preparing an alkaline water-soluble resin is not particularly limited, but the known method may be applied.

In order to sufficiently manifest the effect of the present invention, an acid value of an alkaline water-soluble resin is preferably 15 mgKOH/g or more, more preferably 30 mgKOH/g or more, further preferably 50 mgKOH/g or more, particularly preferably 70 mgKOH/g or more, most preferably 70 to 500 mgKOH/g or more.

A thermoplastic resin which can be used in the present invention is not particularly limited as far as a methanol index is 20 or more. A methanol index of an alkaline water-soluble resin (M) obtained in Examples described later is 200 or more. Upon measurement of the methanol index, as an alkaline-soluble resin (M), a powder obtained by removing a solvent by a rotary evaporator at 80° C., drying this with a dryer at 100° C., pulverizing this using a vibration mill, and passing through a JIS 200 μm sieve was used.

There is no problem if the hydrophobic substance is used in the state where dispersed in water or other liquid, by using an appropriate agent. In addition, also when the hydrophobic substance is blended in a water-absorbent resin together with a substance other than a hydrophobic substance, for example, a hydrophilic substance, if a sum of a methanol index of a hydrophobic substance and that of a hydrophilic substance is 20 or more, the substance can be used without any problem.

(III) Process for Preparing a Waste Solution Solidifying Agent

A process for preparing a waste solution solidifying agent of the present invention is a process of preparing a particulate waste solution solidifying agent containing, as an essential component, a water-absorbent resin particle having a crosslinked structure obtained by polymerizing a water-soluble ethylenic unsaturated monomer, and comprises a step of mixing a non-volatile hydrophobic substance having the following methanol index of 20 or more after polymerization.

Methanol Index: when 1 g of a hydrophobic substance is added to 50 ml of pure water at 25° C., in the case where this hydrophobic substance is a solid, a volume (ml) of methanol at 25° C. necessary for wetting this, or in the case where this hydrophobic substance is a liquid, a volume (ml) of methanol at 25° C. necessary for dispersing and/or emulsifying this.

The waste solution solidifying agent of the present invention is a particulate treating agent used in a method of treating a waste solution by placing the treating agent into a waste solution to solidify the waste solution into a gel, and is characterized by comprising, as an essential component, a water-absorbent resin having a crosslinked structure obtained by polymerizing a water-soluble ethylenic unsaturated monomer, wherein when placed in a 0.90 mass % aqueous sodium chloride solution at once, 20 to 95 mass % of the agent is floated, and 80 to 5 mass of the agent is settled. A process such as adjustment of a density of a water-absorbent resin by foaming or granulation is not particularly limited as far as such the characteristic is possessed, but preferably, it is better to use a waste solution solidifying agent by a process using the hydrophobic substance, that is, a process for preparing a waste solution solidifying agent of the present invention. A process for preparing a waste solution solidifying agent of the present invention is based on the following finding. That is, a true density of a water-absorbent resin depends on its monomer, and is about 1.6 g/cm$^3$ in the case of a polymer from sodium acrylate, and the resin is not floated in a physiological saline (density; about 1.0 g/cm$^3$) based on its true density. However, when a particular hydrophobic substance is used in the present invention, it was found that a water-absorbent resin having a true density of 1.6 g/cm$^3$ is floated in a physiological saline (density; about 1.0 g/cm$^3$), and a part is settled.

In a step of mixing a hydrophobic substance in a process for preparing a waste solution solidifying agent of the present invention, a process is not particularly limited as far as a hydrophobic substance having a methanol index of 20 or more and a water-absorbent resin can be substantially solidified, but examples include any of the following 1 to 7 methods.

1. A method of dispersing a hydrophobic substance in a monomer solution containing an inner crosslinking agent at polymerization of a water-absorbent resin, polymerizing it and, if necessary, drying and pulverizing this to prepare a particulate waste solution solidifying agent.

2. A method of surface crosslinking-treating a vicinity of a surface of the water-absorbent resin obtained in the above 1 to prepare a particulate waste solution solidifying agent.

3. A method of polymerizing a monomer solution containing an inner crosslinking agent at polymerization of a water-absorbent resin and, if necessary, drying and pulverizing this to obtain a water-absorbent resin (1), and adding a hydrophobic substance, followed by mixing, to prepare a particulate waste solution solidifying agent (1).

4. A method of preparing a particulate waste solution solidifying agent by dispersing a hydrophobic substance in a surface crosslinking agent when a part near a surface of the water-absorbent resin (1) obtained in 3 is surface crosslinking-treated.

5. A method of surface crosslinking-treating a vicinity of a surface of the particulate waste solution solidifying agent (1) obtained in the above 3 to prepare a particulate waste solution solidifying agent.

6. A method of surface crosslinking-treating a vicinity of a surface of the water-absorbent resin (1) obtained in the above 3 to obtain a water-absorbent resin (2), and adding a hydrophobic substance, followed by mixing, to prepare a particulate waste solution solidifying agent.

7. A method of preparing a particulate waste solution solidifying agent by adding and mixing a hydrophobic substance in a cooling step after a part near a surface of the water-absorbent resin is surface crosslinking-treated to obtain a water-absorbent resin (2) after a monomer solution containing an inner crosslinking agent at polymerization of a water-absorbent resin is polymerized and, if necessary, dried and pulverized.

In the aforementioned methods 1 to 7, a hydrophobic substance may be added to a monomer at polymerization of the water-absorbent resin in the above 1 to 2, but in order to realize the state where the hydrophobic substance is uniformly attached to a surface of the water-absorbent resin, preferable are the methods 3 to 7. More preferable are the methods 4 to 7 in which surface crosslinking treatment is performed.

A hydrophobic substance used in the present invention is as described above, and comprises a hydrophobic substance having a methanol index of 20 or more, and is such that, by substantial fixation, preferably, by attachment to a surface of a water-absorbent resin, when a water-absorbent resin is placed into a waste solution, at least a part of a water-absorbent resin can be floated on an upper surface of a waste solution, and a remainder can be settled.

(Mixing Method)

When the hydrophobic substance used in the present invention is a powder, a method of directly mixing a hydrophobic substance as a powder into a water-absorbent resin such as a dry blending method, a procedure of dispersing into a surface crosslinking agent solution in which the surface crosslinking agent, water and, if necessary, a hydrophilic organic solvent are mixed, in a slurry manner, and mixing this into a water-absorbent resin, or a procedure of dispersing the hydrophobic substance into water or a hydrophilic organic solvent in a slurry manner, and mixing this into a water-absorbent resin is used.

When the hydrophobic substance is dispersed in a slurry manner, and mixing this into a water-absorbent resin, an amount of water, or an aqueous solution comprising water and a hydrophilic organic solvent which are used as necessary, to be added, has a different optimal amount depending on a kind and a particle size of a water-absorbent resin and, in the case of water, is usually 10 mass parts or smaller, preferably in a range of 1 to 5 mass parts relative to 100 mass parts of a solid matter of a water-absorbent resin. In addition, an amount of a hydrophilic organic solvent to be used is, similarly, usually 10 mass parts or smaller, preferably in a range of 0.1 to 5 mass parts relative to 100 mass parts of a solid matter of a water-absorbent resin. In addition, a concentration of the hydrophobic substance in the slurry is appropriately selected depending on a kind of the hydrophobic substance and a dispersing medium to be used, and a viscosity of a slurry, and is not particularly limited. The concentration is usually in a range of 0.001 to 30 mass %, preferably in a range of 0.01 to 10 mass %. The hydrophobic substance and a powder of a water-absorbent resin are mixed usually at a temperature of room temperature or higher, and in order to obtain stable liquid absorbing property of a particulate waste solution solidifying agent, and flowability at moisture absorption, they are mixed at preferably 40 to 180° C., more preferably 50 to 100° C.

In the process for preparing a waste solution solidifying agent of the present invention, an amount of the hydrophobic substance to be added is different depending on such as a blood concentration in a waste solution, and it is desirable that a content of a hydrophobic substance is in a range of 0.001 to 10 mass %, preferably in a range of 0.01 to 1 mass %, more preferably in a range of 0.03 to 0.7 mass %, most preferably in a range of 0.03 to 0.5 mass % relative to a total water-absorbent resin particle. When an amount of a hydrophobic substance to be added is less than 0.001 mass %, floating upon placement of a waste solution solidifying agent into a waste solution is insufficient and, as a result, since settlement of a waste solution solidifying agent is accelerated, a time until solidification of a whole waste solution becomes longer. On the other hand, when an amount of a hydrophobic substance to be added exceeds 10 mass %, settlement upon placement of a waste solution solidifying agent into a waste solution becomes insufficient, and a time until solidification of a whole waste solution becomes longer.

As an apparatus used when a liquid containing a water-absorbent resin and a hydrophobic substance, a powder and/or a slurry solution are mixed in the present invention include normal apparatuses such as a cylindrical mixer, a screw-type mixer, a screw-type extruder, a turbilizer, a Nauta-type mixer, a V-type mixer, a ribbon-type mixer, a twin arm-type kneader, a flowing-type mixer, and air stream-type mixer, a rotating disk-type mixer, a roll mixer, and a rolling mixer. A rate of mixing may be high or low. These mixers may be used for mixing a surface crosslinking agent in the aforementioned surface crosslinking of a water-absorbent resin.

(Hydrophilic substance)

Various hydrophilic substances may be further added to the water-absorbent resin and/or waste solution solidifying agent, provided that a sum of a methanol index of a hydrophobic substance and a hydrophilic substance as a mixture is 20 or more.

Examples of a hydrophilic substance having a methanol index of less than 20 specifically include metal oxide such as silicon dioxide and titanium oxide, silicic acid (salt) such as natural zeolite and synthetic zeolite, inorganic compounds such as kaolin, talc, clay and bentonite, and other organic compounds. Among them, silicon dioxide and silicic acid (salt) are more preferable, and silicon dioxide and silicic acid (salt) having an average particle diameter measured by a coulter counter method of 200 μm or smaller (e.g. Aerosil 200 manufactured by Nippon Aerosil Co., Ltd.) are further preferable.

An amount thereof to be used depends on a combination of a water-absorbent resin and/or a waste solution solidifying agent and a hydrophilic substance, preferably an inorganic powder, and is 0.001 to 5 mass parts, more preferably 0.01 to 3 mass parts relative to 100 mass parts of a water-absorbent resin and/or a waste solution solidifying agent. Depending on desired liquid absorbing property and a particle size of a waste solution solidifying agent, when the amount exceeds the aforementioned range is used, there is a possibility that it becomes difficult to prevent reduction in liquid absorption property when an impact force is given.

A method of mixing a water-absorbent resin and/or a waste solution solidifying agent and a hydrophilic substance, preferably an inorganic powder is not particularly limited, but for example, a dry blending method of mixing powders, and a wet mixing method can be adopted, and a dry blending method is more preferable.

(Other Substances)

A hydrophobic or hydrophilic substance used in the present invention is not limited to the aforementioned substances, but substances having a methanol index of less than 20 or not less than 20 may be appropriately used.

The aforementioned process for preparing the waste solution solidifying agent of the present invention may comprise a step of imparting various functions, such as addition of a deodorizing agent, an antibacterial agent, a perfume, a foaming agent, a pigment, a dye, a plasticizer, an adhesive, a surfactant, a fertilizer, an oxidant, protein cross-linking agent, a reducing agent, water, salts, a chelating agent, a bactericide, a hydrophilic polymer such as polyethylene glycol and polyethylenimine, or a thermosetting resin such as a polyester resin and a urea resin, if necessary. An amount of these hydrophobic or hydrophilic substances to be used is usually 0 to 30 mass parts, preferably in a range of 0 to 10 mass parts, more preferably in a range of 0 to 1 mass part relative to 100 mass parts of a water-absorbent resin.

By adopting the aforementioned respective essential features, a time for solidifying a medical waste solution containing blood, body fluid or the like can be remarkably shortened. In particular, a time for solidifying a medical waste solution containing blood, body fluid or the like in a vertically oriented waste solution canister can be remarkably shortened.

(IV) Waste Solution Solidifying Agent

The waste solution solidifying agent of the present invention obtained, for example, by the aforementioned process is a waste solution solidifying, agent which is the aforementioned particulate treating agent used in a method of treating a waste solution by placing a treating agent into a waste solution to solidify the waste solution into a gel, and is characterized by comprising, as an essential component, a water-absorbent resin having a crosslinked structure obtained by polymerizing a water-soluble ethylenic unsaturated monomer, wherein, when placed into a 0.90 mass % aqueous sodium chloride solution at once, 20 to 95 mass % of the agent is floated, and 80 to 5 mass % of the agent is settled. In this respect, 'floating and settlement were defined by the state at one minute after placement of 40 g of a particulate waste solution solidifying agent at once into a measuring cylinder of an effective volume of 1000 ml (inner diameter 66 mm) which stands with a vertical axial direction and contains 1000 ml of a 0.90 mass % aqueous sodium chloride solution at 25° C.

In addition, a preferable aspect of the waste solution solidifying agent of the present invention is a particulate waste solution solidifying agent containing, as an essential component, a water-absorbent resin having a crosslinked structure obtained by polymerizing a water-soluble ethylenic unsaturated monomer, which further contains a hydrophobic substance having the following methanol index of 20 or more in addition to a water-absorbent resin.

Methanol index: when 1 g of a hydrophobic substance is added to 50 ml of pure water at 25° C., in the case where this hydrophobic substance is a solid, a volume (ml) of methanol at 25° C. necessary for wetting this, or in the case where this hydrophobic substance is a liquid, a volume (ml) of methanol at 25° C. necessary for dispersing and/or emulsifying this.

In these waste solution solidifying agents, preferably, the hydrophobic substance is contained on a surface of a water-absorbent resin at 0.001 to 10 mass % (relative to water-absorbent resin). The aforementioned waste solution solidifying agent, a part of which is settled, usually refers to a waste solution part, that is, as aforementioned, 5 to 80 mass % s of a settling substance, but a part of floating substance is included.

(1) Content of Water-Absorbent Resin

A content of a water-absorbent resin is usually 50 to 100 mass %, preferably 70 to 99 mass %, further preferably 80 to 98 mass % in a waste solidifying agent. As a minor component other than a water-absorbent resin, the aforementioned hydrophobic substance and water are preferably used.

(2) Solidifying Agent Floating Rate

The floating state of a waste solution solidifying agent of the present invention is 20 to 95 mass %, preferably 25 to 80 mass %, more preferably 25 to 70 mass % of a total mass of a placed particulate waste solution solidifying agent. The floating state refers to a water-absorbent resin remaining at a part upper than a 500 ml position of a measuring cylinder of an effective volume of 1000 ml (inner diameter 66 mm) at one minute after placement of a waste solution solidifying agent. When the floating state is less than 20 mass %, settlement of a particulate waste solution solidifying agent is accelerated, and since progression of solidification from an upper part of a waste solution becomes insufficient, a time for solidifying a whole waste solution is delayed. On the other hand, when the floating state exceeds 95 mass %, since a settling rate of a particulate waste solution solidifying agent is delayed, and progression of solidification from a lower part of a waste solution becomes insufficient, a time for solidifying a whole waste solution is delayed. A method of measuring a solidifying agent floating amount will be later explained in Examples.

(3) Solidifying Time a) 0.90 Mass % Aqueous Sodium Chloride Solution The waste solution solidifying agent of the present invention contains the hydrophobic substance used in the present invention and the water-absorbent resin used in the present invention and, when 40 g of a waste solution solidifying agent is placed at once into a measuring cylinder of an effective volume of 1000 ml (inner diameter 66 mm) which stands with a vertical axial direction and contains 1000 ml of a 0.90 mass % aqueous sodium chloride solution (physiological saline) at 25° C., a solidification time from placement to solidification of the physiological saline is preferably 60 to 700 seconds.

When a solidification time exceeds 700 seconds, a solidification time is too long, and this is inconvenient in actual use in some cases, and further no solidification is attained in some cases. When a solidification time is less than 60 seconds, a substance becomes non-uniform in some cases. A solidification time is preferably 600 seconds or shorter, more preferably 540 seconds or shorter, further preferably 480 seconds or shorter, particularly preferably 420 seconds or shorter.

This is derived from that the floating state defined by the state at one minute after placement of 40 g of a particulate waste solution solidifying agent at once into a measuring cylinder of an effective volume of 1000 ml (inner diameter 66 mm) which stands with a vertical axial direction and contains 1000 ml of a 0.9 mass % aqueous sodium chloride solution (physiological saline) at 25° C., as described in the "(2) solidifying agent floating rate", is 20 to 95 mass % of a total mass of a placed particulate waste solution solidifying agent. A method of measuring a solidification time will be later described in Examples.

b) 0.90 Mass % Aqueous Sodium Chloride Solution Containing 20 Mass % of Defibered Cattle Blood The waste solution solidifying agent of the present invention contains the hydrophobic substance used in the present invention and the water-absorbent resin used in the present invention and, when 99 g of a waste solution solidifying agent is placed at once in a measuring cylinder of an effective volume 3000 ml (inner diameter 103 mm) which stands with a vertical axial direction and contains 3000 ml of an aqueous solution at 25° C. containing 20 mass % of defibered cattle blood relative to a 0.90 mass % aqueous sodium chloride solution (which may hereinafter be referred to as defibered-cattle-blood-containing physiological saline), a solidification time of from the placement to solidification of the defibered-cattle-blood-containing physiological saline is preferably 5 to 50 minutes.

When a solidification time exceeds 50 minutes, a solidification time is too long, and this is inconvenient in actual use in some cases, and further no solidification is attained in some cases. When a solidification time is less than 5 minutes, a substance becomes non-uniform in some cases. A solidification time is preferably 45 minutes or shorter, more preferably 40 minutes or shorter, further preferably 35 minutes or shorter, particularly preferably 30 minutes or shorter.

A method of measuring a solidification time will be later described in Examples.

(4) Water-Absorbent Resin Distribution after Completion of Solidification

A distribution of a water-absorbent resin after completion of solidification of the waste solution solidifying agent of the present invention is preferably 0 to 6, more preferably 5 or less, further preferably 4 or less as expressed by a standard deviation. Herein, a distribution of a water-absorbent resin after completion of solidification means any of (1) a distribution of a water-absorbent resin after completion of solidification of a 0.90 mass % aqueous sodium chloride solution when 40 g of a waste solution solidifying agent is placed at once in a measuring cylinder of an effective volume 1000 ml (inner diameter 66 mm) which stands with a vertical axial direction and contains 1000 ml of the aqueous solution at 25° C., and (2) a distribution of a water-absorbent resin after completion of solidification of an aqueous solution when 99 g of a waste solution solidifying agent is placed at once into a measuring cylinder of an effective volume 3000 ml (inner diameter 103 mm) which stands with a vertical axial direction and contains 3000 ml of an aqueous solution at 25° C. to which 20 mass % of defibered cattle blood is added to a 0.90 mass % aqueous sodium chloride solution and, in any case of (1) and (2), the distribution is preferably in the aforementioned range of a standard deviation. When a standard deviation exceeds 6, a water-absorbent resin is non-uniformly distributed, and a waste solution does not lead to solidification at a part having a low water-absorbent resin concentration in some cases. In addition, in order that a waste solution leads to complete solidification in such the state, a large amount of a waste solution solidifying agent becomes necessary. A method of measuring a standard deviation of a distribution of a water-absorbent resin will be described later in Examples.

(5) Water Absorption Capacity (CRC)

A water absorption capacity (CRC) of the waste solution solidifying agent of the present invention is usually 10 g/g or more, preferably 25 g/g or more, more preferably 30 g/g or more, further more preferably 35 g/g or more relative to a physiological saline. An upper limit is not particularly limited, but is usually about 100 g/g is sufficient. When a water absorption capacity is low, a large amount of a solidifying agent is necessary, and a solidification time becomes long. A water absorption capacity may be appropriately adjusted by inner crosslinking and surface crosslinking of the water-absorbent resin. A method of measuring water absorption capacity (CRC) will be described later in Examples.

(6) Particle Diameter

The particulate waste solution solidifying agent of the present invention has a particle shape, and a waste solution solidifying agent is such that particles of smaller than 850 μm and not smaller than 106 μm are preferably 90 to 100 mass %, more preferably 95 to 100 mass %, further preferably 98 to 100 mass % of a whole. In addition, a mass average particle diameter of a waste solution solidifying agent is preferably 150 to 700 μm, more preferably 200 to 600 μm, further preferably 300 to 500 μm. Controlling of a particle diameter may be appropriately adjusted by granulation, pulverization, classification, and control of polymerization in reverse phase. In addition, the aforementioned particle diameter may be adjusted at a stage of a water-absorbent resin, therefore, is also a particle diameter of a preferable water-absorbent resin. In addition, by granulation of a water-absorbent resin and a waste solution solidifying agent, a solidification time is further shortened, and floating is adjusted.

When particles of smaller than 106 μm exceeds 10 mass %, diffusibility of blood or urine is inhibited at liquid absorption and, since a contact area with the air is increased upon use, a waste solution solidifying agent is easily solubilized and, when a waste solution solidifying agent is placed into a waste solution, so-called fisheyes are formed on a liquid surface of a waste solution in some cases, which is not preferable. When particles exceeding 850 μm exceeds 10 mass %, a liquid absorption rate of a waste solution solidifying agent is delayed, which is not preferable.

(7) Shape

Figure 2:
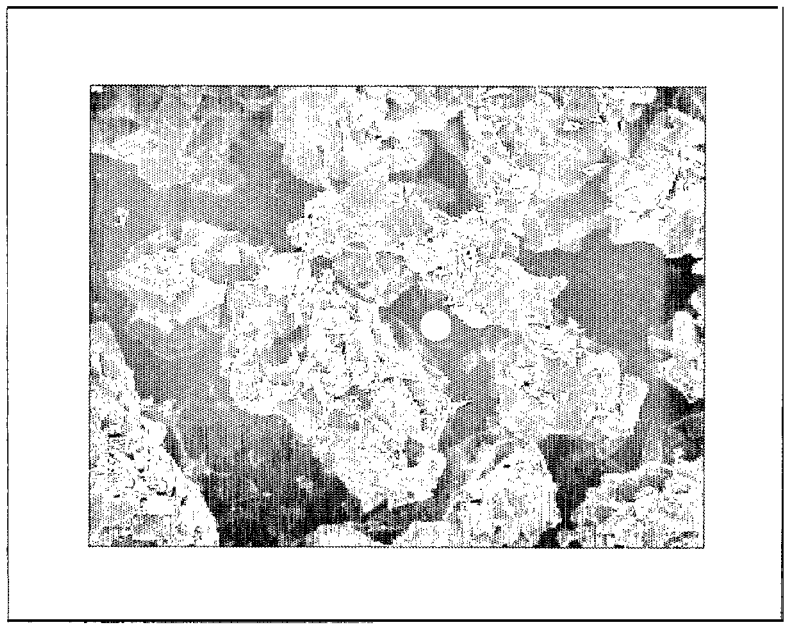
FIG. 2 is a photograph of a waste solution solidifying agent (water-absorbent resin (K)) used in Examples of the present invention.

Examples of a shape thereof include a spherical shape and/or an ellipsoidal shape or a Wiener sausage primary particle shape obtained by reverse phase suspension polymerization described in FIGS. 1 and 2 of U.S. Pat. No. 5,244,735, a shape of a primary particle particulate material in which spherical particles and/or ellipsoidal particles are agglomerated, such as agglomerated beads described in FIG. 1 on page 75 of NON WOVENS WORLD October-November 2000 (published by Marketing Technology Service, Inc.), an irregular shape which is a shape derived from a pulverized substance of a hydrous gel-like polymer obtained by polymerizing an aqueous monomer solution, and a shape of its granulated substance, such as Crystals in FIGS. 2, 3 and 4 of U.S. Pat. No. 5,981,070, and FIG. 1 on page 75 of the aforementioned NON WOVENS WORLD October-November 2000.

A shape of the waste solution solidifying agent of the present invention may be any of a spherical primary particle, an ellipsoidal primary particle, a granulated substance of a spherical particle or an ellipsoidal particle, an irregular shape derived from a pulverized substance of a hydrous gel-like polymer obtained by polymerizing a monomer particle, or a shape of its granulated substance. For shortening a solidification time or adjusting floating, granulation is performed separately or at the same time with surface crosslinking.

(8) Absorption Capacity Under Load (AAP)

It is also preferable that the waste solution solidifying agent of the present invention has an absorption capacity under load of a certain value or larger from a viewpoint of a solidification efficiency. An absorption capacity under load when a load is under pressure of 2.06 kPa and/or 4.83 kPa (under load) is 3 g/g or more, preferably 5 g/g or more, more preferably 10 g/g or more, further preferably 20 g/g or more, most preferably 25 g/g or more. An upper limit is not particularly limited. An absorption capacity under load may be appropriately adjusted, for example, by adjusting the surface crosslinking.

In addition, the waste solution solidifying agent of the present invention is also preferably such that an absorption capacity under load is hardly reduced even when an impact force is given. Whereby, the present invention is characterized in that reduction in performance is small also upon actual use. A retaining index of absorption capacity under load is preferably 0.90 to 1.20, more preferably 0.95 to 1.10. The retaining index of absorption capacity under load and a method of measuring it will be described in Examples. The retaining index of absorption capacity under load may be appropriately adjusted, for example, by adjusting the aforementioned surface crosslinking.

(9) Flowability at Moisture Absorption

Flowability at moisture absorption (hereinafter, simply abbreviated as moisture absorption flowability) is assessment of blocking or caking, and flowability as a powder under allowing to stand at 25° C. or relative humidity of 90% RH. The waste solution solidifying agent of the present invention exhibits neither blocking nor caking, and exhibits excellent characteristic of moisture absorption flowability, in a range of a water content of a waste solution solidifying agent of usually about 10 to 30 mass %. A flowability index of the waste solution solidifying agent of the present invention at moisture absorption is 90 to 100 mass %, preferably 95 to 100 mass %, more preferably 98 to 100 mass %.

In addition, the waste solution solidifying agent of the present invention has the characteristic that it has flowability at moisture absorption which is not reduced even after impartation of an impact force, and has better and stable flowability of a powder. A moisture absorption flowability retaining index of the waste solution solidifying agent of the present invention is 0.90 or more, preferably 0.95 to 1.10, more preferably 0.97 to 1.05. Even when an impact force is given to the waste solution solidifying agent, excellent property having little reduction is exhibited. A method of measuring a flowability index at moisture absorption and a moisture absorption flowability retaining index will be described in detail in Examples.

(10) Powder Property

Since the waste solution solidifying agent of the present invention has little attaching property, and small inner friction coefficient or inner friction angle, a repose angle becomes small not only at moisture absorption but at water content of less than 10%, and characteristic of excellent flowability of a powder is exhibited. The inner friction coefficient or inner friction angle in the powder property can be obtained from a shearing test of a powder layer. As an apparatus for performing a shearing test of a powder, there are a shearing box type, a ring shearing type, and a parallel flat type, for example, Jenike Shear Cell. Since the waste solution solidifying agent of the present invention has the aforementioned powder property, this is useful for simplifying a hopper and a powder storing tank used in a process for preparing the waste solution solidifying agent.

(11) Bulk Density and True Density

A bulk density (defined in U.S. Pat. No. 6,562,879) of the waste solution solidifying agent of the present invention is usually in a range of 0.30 to 0.90 g/cm$^3$, preferably 0.50 to 0.80 g/cm$^3$, further preferably 0.60 to 0.80 g/cm$^3$, and a true density (defined in EP 736060) is usually in a range of 1.1 to 2.0 g/cm$^3$, further 1.2 to 1.8 g/cm$^3$. The waste solution solidifying agent of the present invention has the characteristic that it is floated in water (density 1.0) even when a true density exceeds 1.1 g/cm$^3$.

A bulk density and a true density are appropriately controlled by adjusting a monomer composition (bulk density and true density, particularly true density) or a particle diameter (bulk density). When a bulk density and a true density are outside the aforementioned range, controlling of solidification and floating becomes difficult, and a problem of transport arises in some cases.

(12) Covering Index

In the waste solution solidifying agent of the present invention, it is desirable that, a covering index of a hydrophobic substance on a water-absorbent resin surface is preferably in a range of not less than 0.10 to less than 0.80, more preferably in a range of not less than 0.15 to less than 0.75, further preferably in a range of not less than 0.20 to less than 0.70. When a covering index is 0.80 or more near complete covering, settlement upon placement of a waste solution solidifying agent into a waste solution becomes insufficient, and there is a possibility that a time until solidification of a whole waste solution becomes longer, and a waste solution is not solidified without settling. On the other hand, when a covering index is less than 0.10, floating becomes insufficient upon placement of a waste solution solidifying agent into a waste solution becomes insufficient, and there is a possibility that a time until solidification of a whole waste solution becomes longer. The method for measuring the aforementioned covering index will be later described in detail in Examples.

(V) Waste Solution Solidifying Method

The waste solution solidifying method of the present invention is a method of treating a waste solution by placing a treating agent into a waste solution to solidify the waste solution into a gel, and the aforementioned waste solution solidifying agent of the present invention is used as the treating agent. The waste solution solidifying agent of the present invention can be used for solidifying various waste solutions such as a beverage waste solution, a factory waste solution, a radiation waste solution, and a feces or urine waste solution, an organic substance or a solid dispersion may be contained in a waste solution, and can be preferably used for solidifying a medical waste solution having many previous problems, due to rapid and uniform solidification. A waste solution refers to an aqueous solution or a leaked aqueous solution for waste.

As a solidification method of the present invention, various canister shapes (vertically oriented, laterally oriented etc.) and methods of placing a solidifying agent (simultaneous placement/divided placement into waste solution, pre-placement/post-placement into waste solution) can be widely applied. Due to rapid uniform solidification, the waste solution solidifying agent of the present invention is preferably used for solidifying a waste solution, preferably, in a vertically oriented canister, for example, in a vertically oriented canister (a canister having a 1000 ml measuring cylinder shape described later). Upon placement, the agent may be placed as a powder, or may be placed in the state where a waste solution solidifying agent is placed in a water-soluble, water-disintegrating or water permeable canister or bag.

A part of a particulate waste solution solidifying agent placed in a waste solution is sunk, but since solidification progresses from an upper part and a lower part of a waste solution by floating of the rest of the agent, in particular, when a vertically oriented canister is used, it becomes possible to remarkably shorten a time until solidification of a whole waste solution. In addition, since a floating particulate waste solution solidifying agent is gradually settled, in other words, the agent is settled while absorbing a liquid, the effect of further shortening a time until solidification of a whole waste solution is also exerted.

(VI) Package for Solidifying Waste Solution

A package for solidifying a waste solution of the present invention is characterized in that the waste solution solidifying agent of the present invention is packaged. A shape and a material of a package of the present invention are not particularly limited. As a size of a package, such a size is preferable that 10 to 1,000 g of a waste solution solidifying agent can be sealed, and a waste solution solidifying agent can be taken out therefrom by opening a part thereof, and examples include a poly-widemouthed bottle, and a water-soluble or water-permeable package. Examples of a poly-widemouthed bottle include a poly-widemouthed bottle equipped with soft packaging (e.g. a commercially available bottle described in catalogue 800 manufactured by Teraoka Research Device; material polyethylene).

DETAILED DESCRIPTION OF THE PREFERRED EMBODIMENTS

The present invention will be explained in further detail below by way of Examples and Comparative Examples, but the present invention is not limited to these Examples and the like as far as not going beyond the gist of the present invention. Incidentally, physical properties described in these Examples and Comparative Examples were measured by the following methods (1) to (12). In addition, unless otherwise noted, the unit "part(s)" means mass part(s) (weight part(s)).

(1) Mass Average Particle Diameter

A water-absorbent resin powder or a waste solution solidifying agent was classified with a JIS standard sieve such as 850 μm, 600 μm, 500 μm, 425 μm, 300 μm, 212 μm, 150 μm, 106 μm, and 75 μm and a remaining percentage was plotted on a logarithmic probability paper. Whereby, a mass average particle diameter (D50) was read.

In classification, 10 g was placed in a JIS standard sieve having the aforementioned mesh opening size (The IDA TESTING SIEVE: inner diameter 80 mm) under the condition of room temperature (20 to 25° C.) and a relative humidity of 50% RH, and classified with a Rotap-type sieve shaker (ES-65-type sieve shaker manufactured by IIDASEISAKUSYO Co. Ltd.) for 10 minutes. A mass average particle diameter (D50) is a particle diameter of a standard sieve corresponding to 50% by weight of a whole particle with a standard sieve having a constant mesh opening size as in U.S. Pat. No. 5,051,259.

(2) Water Absorption Capacity (CRC/Centrifuge Retention Capacity)

About 0.20 g (Wp1) of a water-absorbent resin or a waste solution solidifying agent was uniformly placed in a bag (60 mm×60 mm) made of a non-woven fabric, and this was immersed in a 0.9 mass % aqueous sodium chloride solution (physiological saline). After 30 minutes, the bag was pulled out, water was removed at 250 G for 3 minutes using a centrifuge, and a mass Wa (g) was measured. In addition, the same procedure was performed without using a water-absorbent resin or a waste solution solidifying agent and, thereupon, a mass Wb (g) was measured. From these masses Wa and Wb, a water absorption capacity (g/g) of a water-absorbent resin or a waste solution solidifying agent was measured according to the following mathematical equation 1.

$$\text{Water absorption capacity (g/g)} = (\text{mass } Wa \text{ (g)} - \text{mass } Wb \text{(g)} - \text{mass } Wp1 \text{ (g) of water-absorbent resin})/(\text{mass } Wp1 \text{ (g) of water-absorbent resin}) \quad \text{(mathematical equation 1)}$$

(3) Absorption Capacity Under Load (AAP/Absorbency Against Pressure)

Absorption capacity under load (AAP) was measured using an apparatus described in FIG. 1 of Japanese Patent Application No. 2004-029590 or FIG. 6 of WO2005/JP1689. A load 208 adjusted so that a pressure of 2.06 kPa (0.3 psi) and/or 4.83 kPa (0.7 psi) was realized, was prepared. 0.90 g ($Wp2$) of a water-absorbent resin or a waste solution solidifying agent was scattered on a wire net of a plastic cylinder 204 having a diameter of 60 mm in which a wire mesh 202 of 400 mesh (mesh opening size: 38 μm) was attached to a bottom. A liquid absorbing equipment on which the load 208 (0.3 psi and/or 0.7 psi hour) was placed, was placed on a filter paper (filter paper of 90 mm of FILTER PAPER 2 manufactured by ADVANTEC) 212 of a glass filter 210. A value ($Wc$) of a physiological saline absorbed after 60 minutes was measured. An absorption capacity under load was obtained using the following mathematical equation 2.

$$\text{Absorption capacity under load (g/g)} = \text{mass } Wc \text{ (g)} / \text{mass } Wp2 \text{ (g)} \quad \text{(mathematical equation 2)}$$

(4) How to Give Impact Force

In the present invention, regarding how to give an impact force to a water-absorbent resin or a waste solution solidifying agent, using the method described in [0049] to [0053] on page 7 of JP-A-235378/1997 (Kokai), or in column 7, line 60 to column 8, line 26 in U.S. Pat. No. 6,071,976, an impact force B described in the patent was given to a water-absorbent resin or a waste solution solidifying agent.

First, 30.0 g of a water-absorbent resin or a waste solution solidifying agent together with 10.0 g of glass beads having a ball diameter of 6 mm was placed into a canister having an inner volume of 225 ml (mayonnaise bottle manufactured by Nihon Yamamura Glass Co. Ltd., trade name A-29: see U.S. Pat. No. 6,071,976, canister 41 in FIG. 12), the canister was closed, and mounted on a dispersing machine (No488 testing dispersing machine manufactured by Toyo Seiki Seisakusho, Co., Ltd.: U.S. Pat. No. 6,071,976, FIG. 14), and vibration of a vibration rate rotation number of 750 r.p.m. was given for 30 minutes at 100 V/60 Hz using the dispersing machine.

(5) Retaining Index of Absorption Capacity Under Load

The retaining index of absorption capacity under load in the present invention expresses a ratio between absorption capacities under load before and after impact when an impact force of the above (4) is given to a water-absorbent resin or a waste solution solidifying agent, a moisture absorption flowability index of a water-absorbent resin or a waste solution solidifying agent to which an impact force of the above (4) had been given was measured by a method of the above (3), and the index was calculated by the following mathematical equation 3.

$$\text{Retaining index of absorption capacity under load} = Y/X \quad \text{(mathematical equation 3)}$$

Absorption capacity under load before impact force is given: X
Absorption capacity under load after impact force is given: Y (6) Solidification Time a) 0.90 Mass % Aqueous Sodium Chloride Solution A funnel used for measuring an apparent density described in JIS K3362 is positioned at an upper part of a measuring cylinder of an effective volume of 1000 ml (inner diameter 66 mm, height 292 mm, manufactured by Miyahara, described in Daishin Seisakusho catalogue A-1000, code No 1689-11) which stands with a vertical axial direction and contains 1000 ml of a 0.90 mass % aqueous sodium chloride solution at 25° C., so that a lower port of a funnel is situated at a height from a liquid surface of 40 mm, 66 g of a waste solution solidifying agent is calmly placed into a funnel in the state where a lower part of a funnel is opened, and a time until a waste solution does not move even when the measuring cylinder is fallen is adopted as a solidification time.

b) 0.90 Mass % Aqueous Sodium Chloride Solution Containing 20 Mass % Defibered Cattle Blood Defibered cattle blood is obtained by sterilely collecting blood and, immediately thereafter, assuredly defibering with sterile glass beads, and a cattle blood containing no chemical such as a preservative (manufactured by Nippon Biotest Laboratory; Co., Ltd.) was used.

A funnel used for measuring an apparent density described in JIS K3362 is positioned at an upper part of a measuring cylinder of an effective volume of 3000 ml (inner diameter 103 mm, height 462 mm, manufactured by Samplatech, Co., Ltd., described in Daishin Seisakusho catalogue A-1000, code No 3737-01) which stands with a vertical axial direction and contains 3000 ml of an aqueous solution at 25° C. to which 20 mass % of defibered cattle blood has been added to a 0.90 mass % aqueous sodium chloride solution, so that a lower port of a funnel is situated at a height from a liquid surface of 40 mm, 99 g of a waste solution solidifying agent is calmly placed into a funnel in the state where a lower port of is opened, and a time until a waste solution does not move even when the measuring cylinder is fallen is adopted as a solidification time.

(7) Solidifying Agent Floating Rate

As shown in FIG. 1, an acrylic cylindrical molding (having neither bottom nor lid) of a height of 200 mm having the same inner diameter as that of a measuring cylinder (inner diameter 66 mm) of an effective volume of 1000 ml was immersed in a polyethylene bucket of an effective volume of 18 L containing 18 L of a 0.9 mass % aqueous sodium chloride solution at 25° C., in a vertical direction. In addition, as shown in FIG. 1, a jig A (stainless bar of a diameter 2 mm) was attached to the acrylic cylindrical molding so that only a lower part 146 mm (corresponding to 500 ml of a volume of measuring cylinder) of the acrylic cylindrical molding was immersed (the jig A was not fixed to the bucket of an effective volume 18 L). 40 g of a waste solution solidifying agent was placed into the acrylic cylindrical molding at once by the same method as that described in the above (3), the whole acrylic cylindrical molding was scooped up with a mesh opening size JIS 45 μm sieve (inner diameter 76 mm) after one minute and, thereafter, a waste solution solidifying agent in the acrylic cylindrical molding was taken out in the JIS mesh opening size 45 μm sieve (inner diameter 76 mm). Thereupon, a waste solution solidifying agent attached in the acrylic cylindrical molding was scraped down into the JIS mesh opening size 45 μm sieve (inner diameter 76 mm) with a spatula, thereafter, the JIS mesh opening size 45 μm sieve (inner diameter 76 mm) was dried with the hot air at 180° C. for 16 hours, and cooled to room temperature, a mass W1 (g) was measured, and a solidifying agent floating rate (mass %) was calculated by the following mathematical equation 4.

$$\text{Solidifying agent floating rate (mass \%)} = W1 \text{ (g)} / 40 \text{ (g)} \times 100 \quad \text{(mathematical equation 4)}$$

W1: mass (g) after drying of floating solidifying agent (8) Solidifying Agent Concentration Distribution and Standard Deviation after Absorption a) 0.90 Mass % Aqueous Sodium Chloride Solution According to the same manner as that described in a) of the (6), a 0.90 mass % aqueous sodium chloride solution was solidified using a waste solution solidifying agent, and all of a gel situated at a position of 800 to 1000 ml of the measuring cylinder having an effective volume of 1000 ml was sampled. This was transferred to a stainless vat, dried with the hot air at 180° C. for 16 hours, and cooled to room temperature, and a mass WA (g) after drying was measured. Supposing that a mass WB (g) corresponding to reduction in a mass due to drying was all derived from water and, from this, a mass WC (g) of sodium chloride contained in a gel was calculated by the following mathematical equation 5. From this, a content WD (g) of a solidifying agent at a position of 800 to 1000 ml was defined as WA (g)−WC (g).

The same procedure was performed on a gel at a position of 0 to 800 ml and, according to the same manner as that of calculation of a content of a solidifying agent except for a mass of sodium chloride at a position of 800 to 1000 ml, a content WE (g) a solidifying agent at 600 to 800 ml, a content WF (g) of a solidifying agent at 400 to 600 ml, a content WG (g) of a solidifying agent at 200 to 400 ml, and a content WH (g) of a solidifying agent at 0 to 200 ml were calculated.

Next, a concentration distribution (mass %) of a solidifying agent was obtained by the following mathematical equation 6-1.

$$\text{Sodium chloride mass } WC\ (g) = WB\ (g)/0.991 - WB\ (g) \quad \text{(mathematical equation 5)}$$

WB: mass (g) corresponding to reduction in mass due to drying $$\text{Solidifying agent concentration distribution (mass \%)} = (WD\ (g) \text{ or } WE\ (g) \text{ or } WF\ (g) \text{ or } WG\ (g) \text{ or } WH\ (g))/(WD\ (g) + WE\ (g) + WF\ (g) + WG\ (g) + WH\ (g)) \times 100 \quad \text{(mathematical equation 6-1)}$$

In addition, a standard deviation was obtained by the following mathematical equation 6-2.

$$\text{Standard deviation} = \sqrt{[\{\Sigma(X-M)^2\}/n]} \quad \text{(mathematical equation 6-2)}$$

X: solidifying agent concentration distribution value at each position

M: average of concentration distribution (=20)

n: number of solidifying agent concentration distribution value (=5)

b) 0.90 mass % aqueous sodium chloride solution containing 20 mass % defibered cattle blood As defibered cattle blood, the same defibered cattle blood as that of b) of the (6) was used.

According to the same manner as that described in b) of the (6), a waste solution solidifying agent was used to solidify an aqueous solution in which 20 mass % of defibered cattle blood had been added to a 0.90 mass % aqueous sodium chloride solution, and all gel at a position of 3000 to 2400 ml of the measuring cylinder of an effective volume of 3000 ml was sampled. This was transferred to a stainless vat, this was dried with hot air at 180° C. for 16 hours, and cooled to room temperature, and a mass WI (g) after drying was measured. Gels at positions of 2400 to 1800 ml, 1800 to 1200 ml, 1200 to 600 ml, and 600 to 0 ml were subjected to the similar procedure, and masses WJ (g), WK (g), WL (g) and WM (g) after drying were measured, respectively. From masses after drying, a concentration distribution (mass %) of a solidifying agent was obtained by following mathematical equation 6-3.

$$\text{Solidifying agent concentration distribution (mass \%)} = (WI\ (g) \text{ or } WJ\ (g) \text{ or } WK\ (g) \text{ or } WL\ (g) \text{ or } WM\ (g))/(WI\ (g) + WJ\ (g) + WK\ (g) + WL\ (g) + WM\ (g)) \times 100 \quad \text{(mathematical equation 6-3)}$$

In addition, a standard deviation was obtained by the above mathematical equation 6-2 as in a).

(9) Methanol Index 50 ml of pure water at 25° C. and a stirrer chip (length 25 mm×diameter 8 mm, left and right tapered, material: Teflon (registered trademark)) were placed into a glass beaker (inner diameter 78 mm×height 103 mm) having a volume of 300 ml, 1 g of a hydrophobic substance was added thereon, and this was stirred with a stirrer at 750 rpm. When methanol at 25° C. is added dropwise therein with a burette at 10 ml/min, in the case where this hydrophobic substance is a solid, a volume (ml) of methanol at 25° C. necessary for wetting it, and removing (settling) a floating substance on a liquid surface is referred to as methanol index, or in the case where this hydrophobic substance is a liquid, a volume (ml) of methanol at 25° C. necessary for dispersing and/or emulsifying this is referred to as methanol index. Even when a volume of methanol at 25° C. exceeds 200 ml, in the case where a hydrophobic substance is wetted, and a floating substance on a liquid surface is not nullified, or in the case where dispersion or emulsification was impossible, a methanol index was regarded as 200 or more.

In addition, the state where a hydrophobic substance which is a solid is wetted upon measurement of a methanol index in the present invention means the state where there is no floating substance (hydrophobic substance) on a liquid surface, in other words, the state where all hydrophobic substances are floated in a liquid or settled on a bottom of a beaker. The state where, a hydrophobic substance which is a liquid is dispersed and/or emulsified means the state where a liquid is not separated into a methanol layer and a hydrophobic substance layer.

In addition, when a hydrophobic substance together with a hydrophilic substance was used in a waste solution solidifying agent, 1 g of a sample was prepared at a mass ratio of a hydrophobic substance and a hydrophilic substance to be used, and this was used to measure a methanol index.

(10) Flowability Index at Moisture Absorption

About 2 g of a water-absorbent resin or a waste solution solidifying agent which had passed through a JIS 850 μm standard sieve was uniformly scattered in an aluminum cup having a diameter of 52 mm, this was allowed to stand in a constant temperature and constant humidity equipment for 1 hour under the temperature of 25° C. and a relative humidity of 90% RH. After one hour, a water-absorbent resin or a waste solution solidifying agent contained in an aluminum cup was transferred on a JIS 2000 μm standard sieve (The IIDA TESTING SIEVE: inner diameter 80 mm), and classified for 5 seconds under room temperature (20 to 25° C.) and a relative humidity 50% RH using a Rotap-typed sieve shaker (ES-65 type sieve shaker manufactured by IIDA Seisakusho, Co., Ltd.; rotation number 230 r.p.m, impact number 130 r.p.m), and a mass (A g) of a water-absorbent resin or a waste solution solidifying agent which remained on a 2000 μm mesh, and a mass (B g) of a water-absorbent resin or a waste solution solidifying agent which had passed through the mesh was measured. In the present invention, a flowability index at moisture absorption is defined by the following mathematical equation 7, and the index was calculated according to it.

$$\text{Flowability index at moisture absorption (mass \%)} = A\ (g)/(A\ (g) + B\ (g)) \times 100 \quad \text{(mathematical equation 7)}$$

(11) Moisture Absorption Flowability Retaining Index

A moisture absorption flowability retaining index in the present invention expresses a ratio between moisture absorption flowabilities before and after impact when an impact force of the above (4) is given to a water-absorbent resin or a waste solution solidifying agent, a moisture absorption flowability index of a water-absorbent resin or a waste solution solidifying agent to which an impact force of the above (4) had been given was measured by a method of the above (10), and the index was calculated by the following mathematical equation 8.

Moisture absorption flowability retaining
index=Y/X   (mathematical equation 8)

Moisture absorption flowability index before impact force is given: X

Moisture absorption flowability index after impact force is given: Y

(12) Bulk density

A bulk density was measured according to JIS K3362. Specifically, a bulk density was measured using a measuring equipment shown in FIG. 3 of Japanese Patent Application No. 2004-029590 or FIG. 7 of WO 2005/075070 by the following method.

a) A measuring equipment is placed on a stable base, this is kept horizontal by regulating a three-leg screw, a dried funnel 401 is placed on a stand vertically, and a damper 402 is slightly abutted against a lower port to close the port.

b) A cup 403 which has been washed and dried, and a mass of which has been weighed up to 0.1 g is placed beneath funnel 401, then, 100.0 g of a shrunk sample is calmly placed into a funnel 401.

c) A damper 402 is rapidly opened fully, a sample in a funnel 401 is naturally fallen into a cup 403. In the case where a sample is massy and is attached to a funnel 401, a mass is broken with a glass bar in advance. A part projecting from a cup 403 is ground down with a glass bar (diameter about 8 mm, length about 150 mm), and a mass of a cup 403 containing a sample is weighed up to 0.1 g.

And, a bulk density was obtained using the following mathematical equation 9.

$S=(W2-W1)/V$   (mathematical equation 9)

Wherein,
S: bulk density (g/ml)
W2: mass (g) of cup containing sample
W1: mass (g) of empty cup
V: volume (ml) of cup

(13) Covering Index

A polyvalent metal salt on a water-absorbent resin surface before and after addition of a hydrophobic substance was quantified by ESCA, and a covering index was calculated. Thereupon, measurement was performed by conducting Ar ion discharge polishing (hereinafter, abbreviated as spattering) for 3 seconds to extremely slightly cut a water-absorbent resin. As an apparatus, JPS-9000MX manufactured by JEOL was used. An electrically conducting tape was cut into about 1 cm square, this was applied to an about 6 cm×1 cm rectangular sample base, about 0.2 g of a water-absorbent resin was scattered thereon, a water-absorbent resin which had not been adhered to a tape was blown off with a nitrogen gas, and a water-absorbent resin was fixed on a tape to such an extent that a gap was slightly observed with naked eyes. This sample base was placed into a pre-evacuating chamber, and pre-evacuated for 16 hours. Then, using a thermal cathode electron impact type (Kaufman) ion gun (ion beam current 50 mA, ion beam diameter 1.5 mm), spattering was performed for 3 seconds under the conditions of Ar ion acceleration voltage of 500 V, an acceleration current of 8.5 mA, and an Ar gas pressure of $3\times10^{-2}$ Pa. After evacuation of an Ar gas, a sample base was transferred to a sample chamber for measurement, scanning was repeated ten times every atom under conditions (e.g. Ka rays of Mg was used as an excitation X-ray source, an acceleration voltage was set at 10 kV, emission current was set at 10 mA, pass energy of a detector was set at 10 eV, an energy scanning interval was set at 0.1 eV. An inner shell level was set in a range of 1010 to 1034 eV containing a peak assignable to 2p3/2 in Zn, and was set in a range of 1062 to 1082 eV containing a peak assignable to 1s in Na.) adjusted depending on an element to be detected, and a photoelectron spectrum was obtained. An area value (eV*cps) obtained from a spectrum which had been subjected to background correction (performed by Shirley method) was subjected to quantification correction calculation using a relative sensitivity factor provided on an analysis software annexed to an apparatus, and a value of each element was calculated. From the thus obtained Na atom number on a water-absorbent resin surface after covering, and Na atom number of a water-absorbent resin before covering with a hydrophobic substance, a covering index of a hydrophobic substance was obtained by the following mathematical equation 10.

Covering index=1−{(Na atom number on water-absorbent resin surface after covering with hydrophobic substance)/(Na atom number of water-absorbent resin before covering with hydrophobic substance)}   (mathematical equation 10)

Reference Example 1

5.9 g of polyethylene glycol diacrylate (average addition mole number of ethylene oxide 8) was dissolved in 5500 g of an aqueous sodium acrylate solution (monomer concentration 38 mass %) having a neutralization rate of 65 mol %, and the solution was used as a reaction solution. Then, this reaction solution was degassed for 30 minutes under the nitrogen gas atmosphere. Then, the reaction solution was supplied to a reactor formed by attaching a lid to a stainless twin-arm type kneader with a jacket of an internal volume of 10 L which had two sigma-type wings, and the system was replaced with a nitrogen gas while maintaining the reaction solution at 30° C. Subsequently, 2.46 g of sodium persulfate and 0.10 g of L-ascorbic acid were added while stirring the reaction solution, and polymerization was started about one minute later. And, polymerization was performed at an upper limit and a lower limit of 30° C. to 90° C., and at 60 minutes after polymerization initiation, a hydrous gel-polymer was taken out.

In the resulting hydrous gel-like polymer, a diameter thereof was reduced to about 5 mm. This finely divided hydrous gel-like polymer was spread on a 50 mesh (mesh opening size: 300 μm) wire net, and dried with the hot air at 150° C. for 90 minutes. Then, a dried substance was pulverized using a vibration mill and further classified and compounded according to JIS 850 μm to obtain an irregularly pulverized shape water-absorbent resin (A). Into 100 parts of the resulting water-absorbent resin (A) was mixed a surface crosslinking agent comprising 0.5 parts of propylene glycol, 0.3 parts of 1,4-butanediol, and 3 parts of water. The mixture was heat-treated at 200° C. for 45 minutes to obtain a water-absorbent resin (B).

Reference Example 2

5.9 g of polyethylene glycol diacrylate (average addition mol number of ethylene oxide 8) was dissolved in 5500 g of an aqueous sodium acrylate solution (monomer concentration 38 mass %) having a neutralization rate of 65 mol %, and the solution was used as a reaction solution. Then, this reaction solution was degassed for 30 minutes under the nitrogen gas atmosphere. Then, the reaction solution was supplied to a reactor formed by attaching a lid to a stainless twin-arm type kneader with a jacket having an inner volume of 10 L which had two sigma-type wings, and the system was replaced with a nitrogen gas while maintaining the reaction solution at 30° C. Subsequently, 2.46 g of sodium persulfate and 0.10 g of L-ascorbic acid were added while stirring the reaction solution, and polymerization was initiated about 1 minute later. And, polymerization was performed at an upper limit and a lower limit of 30° C. to 90° C. and, at 60 minutes after polymerization initiation, a hydrous gel-like polymer was taken out.

In the resulting hydrous gel-like polymer, a diameter thereof was reduced to about 5 mm. This finely divided hydrous gel-like polymer was spread on a 50 mesh (mesh opening size: 300 μm) wire net, and this was dried with the hot air at 150° C. for 90 minutes. Then, a dried substance was pulverized using a vibration mill, and classified and compounded according to JIS 500 μm to obtain an irregularly pulverized shape water-absorbent resin (C). Into 100 parts of the resulting water-absorbent resin (C) was mixed a surface crosslinking agent comprising 0.7 parts of glycerin, 2 parts of water, and 0.5 parts of isopropyl alcohol. The mixture was heat-treated at 200° C. for 45 minutes to obtain a water-absorbent resin (D).

Reference Example 3

1.0 L of cyclohexane was placed into a 2 L four-neck separable flask equipped with a stirrer, a refluxing condenser, a thermometer, a nitrogen gas introducing tube and an addition funnel, 4.0 g of sucrose fatty acid ester (manufactured by Dai-ichi Kogyo Seiyaku Co., Ltd., DK-ester F-50, HLB=6) as a dispersant was added to dissolve the material, and a nitrogen gas was blown therein to expel dissolved oxygen. Separately, 84.6 g of sodium acrylate, 21.6 g of acrylic acid and 0.016 g of N,N'-methylenebisacrylamide were dissolved in 197 g of ion-exchanged water, 0.53 g of hydroxyethyl cellulose (manufactured by Daicel Chemical Industries, Co., Ltd., HEC-Daicel EP-850) was further dissolved, to prepare an aqueous monomer solution having a monomer concentration of 35 mass %, and a viscosity of 40 cps. 0.15 g of potassium persulfate was added to this aqueous monomer solution to dissolve the material, and nitrogen gas was blown therein to expel oxygen dissolved in an aqueous solution. Then, an aqueous monomer solution in this flask was added to the separable flask, and this was stirred at 230 rpm to disperse the material. Thereafter, a bath temperature was raised to 60° C. to initiate a polymerization reaction, and a temperature was maintained at this temperature for 2 hours to complete the polymerization. After completion of polymerization, water in a hydrous gel was distilled off by azeotropic dehydration with cyclohexane, this was filtered, and dried at 80° C. under reduced pressure to obtain a spherical polymer powder (E). A water content of the resulting polymer powder (E) was 5.6%. Into 100 parts of the polymer powder (E) mixed a treating solution comprising 0.3 parts of diethylene glycol, 4 parts of water, and 0.5 parts of isopropanol with a paddle-type mixer. At mixing, a great mass was not generated at all, and the mixture was passed through a JIS 850 μm standard sieve, and all of the mixture passed. The resulting mixture was heat-treated with a paddle drier at 180° C. for 1 hour, to obtain a water-absorbent resin (F).

Reference Example 4

1.0 L of cyclohexane was taken in a 2 L four-neck separable flask equipped with a stirrer, a refluxing condenser, a thermometer, a nitrogen gas introducing tube and an addition funnel, 4.0 g of sucrose fatty acid ester (manufactured by Dai-ichi Kogyo Seiyaku Co., Ltd., DK ester F-50, HLB=6) as a dispersant was added to dissolve it, and a nitrogen gas was blown therein to expel dissolved oxygen. Separately, 84.6 g of sodium acrylate, 21.6 g of acrylic acid and 0.016 g of N,N'-methylenebisacrylamide were dissolved in 197 g of ion-exchanged water in a flask, and 0.53 g of hydroxyethyl cellulose (manufactured by Daicel Chemical Industries, Co., Ltd., HEC-Daicel EP-850) was further dissolved to prepare an aqueous monomer solution having a monomer concentration of 35 mass % and a viscosity of 40 cps. 0.15 g of potassium persulfate was added to this aqueous monomer solution to dissolve it, and a nitrogen gas was blown into the aqueous solution to expel dissolved oxygen therein. Then, an aqueous monomer solution in this flask was added to the separable flask, and this was stirred at 230 rpm to disperse it. Thereafter, a bath temperature was raised to 60° C., a polymerization reaction was initiated, and a temperature was retained at this temperature for 2 hours to complete the polymerization. To this polymerization solution was added 1.75 g of wet milling silicon dioxide (Tokusil NP: manufactured by Tokuyama, Co., Ltd.), water and hexane were removed by distillation, and this was dried at 80° C. under reduced pressure to obtain a grape-bunch-shaped polymer powder (G). A water content of the resulting polymer powder (G) was 5.6%. Into 100 parts of a polymer powder (G) was mixed a treating solution comprising 0.3 parts of diethylene glycol, 4 parts of water and 0.5 parts of isopropanol with a paddle-type mixer. At mixing, a great mass was not generated at all, the mixture was passed through a JIS 850 μm standard sieve, and all of the mixture passed. The resulting mixture was heat-treated with a paddle drier at 180° C. for 1 hour to obtain a water-absorbent resin (H).

Reference Example 5

75 g of pure water was added to 500 g of an irregularly pulverized shape water-absorbent resin (B) described in Reference Example 1, the materials were mixed at 330 rpm for 10 minutes using a Lodige mixer (type M5R manufactured by Gebrüder Lödige Maschinenbau GmbH), and dried at 80° C. for 60 minutes in a dryer.

A dried substance was pulverized using a vibration mill, classified with a JIS 850 μm sieve, and compounded to obtain a granulated irregular-shape water-absorbent resin Reference Example 6

A water-absorbent resin (A) described in Reference Example 1 was classified with a JIS 150 μm sieve, to 300 g of a water-absorbent resin (J) which had passed through the sieve was added 420 g of hot water, the materials were mixed at 330 rpm for 2 minutes using a Lödige mixer (type M5R manufactured by Gebrüder Lödige Maschinenbau GmbH), and then dried at 180° C. for 60 minutes in a dryer. A dried substance was pulverized using a vibration mill, classified with a JIS 850 μm sieve, and compounded to obtain a granulated irregular-shape water-absorbent resin (K). A photograph of the water-absorbent resin (K) is shown in FIG. 2.

Into 100 g of a water-absorbent resin (K) was mixed a surface crosslinking agent comprising 0.5 part of propylene glycol, 0.3 part of 1,4-butanediol and 3 parts of water, and the mixture was heat-treated at 200° C. for 45 minutes to obtain a water-absorbent resin (L).

Reference Example 7

An alkaline water-soluble resin was prepared by the following method. That is, a tank-type reactor of a volume of 100

L equipped with a thermometer, a stirring wing, a refluxing condenser and an addition device was charged with 1.8 kg of acrylic acid, 10.2 kg of ethyl acrylate, 24 g of 2,2'-azobis-(2,4-dimethylvaleronitrile) as a polymerization initiator, and 28 kg of methanol as a solvent. On the other hand, an addition device was charged with a mixed solution comprising 2.7 kg of acrylic acid, 5.4 kg of methyl acrylate, 9.9 kg of methyl methacrylate, 66 g of 2,2'-azobis-(2,4-dimethylvaleronitrile) and 2 kg of methanol. Then, a methanol solution in the reactor was heated to 65° C. in the nitrogen gas atmosphere while stirring, followed by a reaction for 20 minutes. Thereby, a polymerization conversion of a content was regulated to be 72%. Subsequently, the aforementioned mixed solution was evenly added dropwise from an addition device over 2 hours while maintaining an inner temperature at 65° C. After completion of addition, 60 kg of methyl ethyl ketone was mixed into a content, thereby, a 25 mass % solution of an alkaline water-soluble resin (M) (hereinafter, the alkaline water-soluble resin (M) is referred to ASP in some cases) was obtained.

An acid value of the resulting alkaline water-soluble resin (M) was 117 mgKOH/g, a weight average molecular weight Mw of the alkaline water-soluble resin (M) was 156,000, and a number average molecular weight Mn was 69,000. Further, when analyzed with a differential scanning calorimeter, a glass transition temperature (Tg) was observed at 10° C. and 67° C. In addition, solubility of the alkaline water-soluble resin (M) in ion-exchanged water at 25° C. was less than 0.5 mass %, and alkaline water solubility (solubility in alkaline water) was 100 mass %.

Example 1

0.1 mass % of zinc stearate (manufactured by Kanto Kagaku, Co., Ltd., deer first grade) relative to 100 parts of a water-absorbent resin (A) was placed into a Lödige mixer (manufactured by Gebrüder Lodige Maschinenbau GmbH, type: M5R) under 25° C. and a relative humidity of 50% RH, and this was stirred at 330 rpm for 90 seconds to obtain a waste solution solidifying agent (1).

Using 40 g of a waste solution solidifying agent (1), a solidification time and a solidifying agent floating rate when 1000 ml of a 0.90 mass % aqueous sodium chloride solution at 25° C. placed into a measuring cylinder having an effective volume of 1000 ml (inner diameter 66 mm) was solidified, were measured. Further, a concentration distribution of a waste solution solidifying agent in a measuring cylinder, and a standard deviation thereof were obtained. Results are shown in Table 1.

In addition, a 0.90 mass % aqueous sodium chloride solution containing 20 mass % of defibered cattle blood was solidified similarly, a solidification time was measured, and a concentration distribution of a waste solution solidifying agent in a measuring cylinder, and a standard deviation thereof were obtained. Results are shown in Table 2.

A waste solution solidifying agent (1) was filled into a poly-widemouthed bottle equipped with a soft package (material polyethylene, described in catalogue 800 of Teraoka Research Device, inner amount 200 cc). When a solidification test was performed, a predetermined amount of a waste solution solidifying agent was filled, from which all amount of a waste solution solidifying agent was placed into a funnel The same procedure was performed also regarding Example 2 to 19 and Comparative Examples 1 to 4.

Example 2

According to the same manner as that of Example 1 except that a water-absorbent resin (A) was changed to a water-absorbent resin (B), a waste solution solidifying agent (2) was obtained.

Using 40 g of a waste solution solidifying agent (2), a solidifying time and a solidifying agent floating rate when 1000 ml of a 0.90 mass % aqueous sodium chloride solution at 25° C. placed in a measuring cylinder having an effective volume of 1000 ml (inner diameter 66 mm) was solidified, were measured. Further, a concentration distribution of a waste solution solidifying agent in a measuring cylinder, and a standard deviation thereof were obtained. Results are shown in Table 1.

In addition, a 0.90 mass % aqueous sodium chloride solution containing 20 mass % of defibered cattle blood was solidified similarly, a solidification time was measured, and a concentration distribution of a waste solution solidifying agent in a measuring cylinder, and a standard deviation thereof were obtained. Results are shown in Table 2.

Example 3

The same procedure as that of Example 2 was performed except that 0.10 mass % of zinc stearate was changed to 0.2 mass % of hydrophobic silicon dioxide (trade name Aerosil R972; manufactured by Nippon Aerosil Co., Ltd.). Thereby a waste solution solidifying agent (3) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

Example 4

The same procedure as that of Example 2 was performed except that 0.10 mass % of zinc stearate was changed to 0.20 mass % of zinc stearate and 0.2 mass % of hydrophilic silicon dioxide (trade name Aerosil 200; manufactured by Nippon Aerosil Co., Ltd.). Thereby a waste solution solidifying agent (4) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

Example 5

The same procedure as that of Example 2 was performed except that 0.1 mass % of zinc stearate was changed to 4.00 mass % of fine powder polyethylene (trade name FLO-THENE F-1.5 manufactured by Sumitomo Seika Chemicals Co., Ltd.). Thereby a waste solution solidifying agent (5) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

Example 6

The same procedure as that of Example 2 was performed except that 0.10 mass % of zinc stearate was changed to 0.15 mass % of zinc myristate (trade name Powder Base M manufactured by Nippon Oil & Fats Co., Ltd.). Thereby a waste solution solidifying agent (6) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

Example 7

The same procedure as that of Example 2 was performed except that 0.10 mass % of zinc stearate was changed to 0.15 mass % of calcium stearate (trade name Japanese Pharmacopoeia calcium stearate, manufactured by Nippon Oil & Fats Co., Ltd.). Thereby a waste solution solidifying agent (7) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

Example 8

The same procedure as that of Example 2 was performed except that 0.1 mass % of zinc stearate was changed to 0.60 mass % of erucic acid amide manufactured by Tokyo Kasei Kogyo Co., Ltd.). Thereby a waste solution solidifying agent (8) was obtained. Erucic acid amide was ground with a mortar, and passed through a JIS 200 μm sieve to obtain a powder, which was used. Thereupon, a solidification time when 1000 ml of a 0.90 mass % aqueous sodium chloride solution placed at 25° C. in a measuring cylinder having an effective volume of 1000 ml (inner diameter 66 mm) was solidified, was measured. Results are shown in Table 1.

Example 9

The same procedure as that of Example 2 was performed except that 0.10 mass % of zinc stearate was changed to 0.40 mass % of stearyl stearate (trade name; Unister M-9676, manufactured by Nippon Oil & Fats Co., Ltd.). Thereby a waste solution solidifying agent (9) was obtained. Stearyl stearate was ground with a mortar, and passed through a JIS 200 μm sieve to obtain a powder, which was used. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

Example 10

The same procedure as that of Example 2 was performed except that a water-absorbent resin (B) was changed to a water-absorbent resin (D). Thereby a waste solution solidifying agent (10) was obtained. Thereupon, a solidification time when 1000 ml of 0.90 mass % aqueous sodium chloride solution at 25° C. placed in a measuring cylinder having an effective volume of 1000 ml (inner diameter 66 mm) was solidified, was measured. Results are shown in Table 1.

Example 11

The same procedure as that of Example 2 was performed except that a water-absorbent resin (B) was changed to a water-absorbent resin (E). Thereby a waste solution solidifying agent (11) was obtained. Thereupon, a solidification time when 1000 ml a 0.90 mass % aqueous sodium chloride solution at 25° C. placed in a measuring cylinder having an effective volume of 1000 ml (inner diameter 66 mm) was solidified, was measured. Results are shown in Table 1.

Example 12

The same procedure as that of Example 2 was performed except that a water-absorbent resin (B) was changed to a water-absorbent resin (F). Thereby a waste solution solidifying agent (12) was obtained. Thereupon, a solidification time when 1000 ml a 0.90 mass % aqueous sodium chloride solution at 25° C. placed in a measuring cylinder having an effective volume of 1000 ml (inner diameter 66 mm) was solidified, was measured. Results are shown in Table 1.

Example 13

The same procedure as that of Example 2 was performed except that a water-absorbent resin (B) was changed to a water-absorbent resin (G). Thereby a waste solution solidifying agent (13) was obtained. Thereupon, a solidification time when 1000 ml a 0.90 mass % aqueous sodium chloride solution at 25° C. placed in a measuring cylinder having an effective volume of 1000 ml (inner diameter 66 mm) was solidified, was measured. Results are shown in Table 1.

Example 14

The same procedure as that of Example 2 was performed except that a water-absorbent resin (B) was changed to a water-absorbent resin (H). Thereby a waste solution solidifying agent (14) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.
In addition, a 0.90 mass % aqueous sodium chloride solution containing 20 mass % of defibered cattle blood was solidified similarly, a solidification time was measured, and a concentration distribution of a waste solution solidifying agent in a measuring cylinder, and a standard deviation thereof were obtained. Results are shown in Table 2.

Example 15

The same procedure as that of Example 2 was performed except that a water-absorbent resin (B) was changed to a water-absorbent resin (I). Thereby a waste solution solidifying agent (15) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Further, a concentration distribution of a waste solution solidifying agent in a measuring cylinder, and a standard deviation thereof were obtained. Results are shown in Table 1.
In addition, a 0.90 mass % aqueous sodium chloride solution containing 20 mass % of defibered cattle blood was solidified similarly, a solidification time was measured, and a concentration distribution of a waste solution solidifying agent in a measuring cylinder, and a standard deviation thereof were obtained. Results are shown in Table 2.

Example 16

The same procedure as that of Example 2 was performed except that a water-absorbent resin (B) was changed to a water-absorbent resin (K). Thereby a waste solution solidifying agent (16) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

In addition, a 0.90 mass % aqueous sodium chloride solution containing 20 mass % of defibered cattle blood was solidified similarly, a solidification time was measured, and a concentration distribution of a waste solution solidifying agent in a measuring cylinder, and a standard deviation thereof were obtained. Results are shown in Table 2.

Example 17

The same procedure as that of Example 2 was performed except that a water-absorbent resin (B) was changed to a water-absorbent resin (L). Thereby a waste solution solidifying agent (17) was obtained. Thereupon, a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

Example 18

According to the same manner as that of Example 2 except that the water-absorbent resin (B) was changed to a mixture comprising 50 mass % of a water-absorbent resin (B) and 50 mass % of a water-absorbent resin (L), the same procedure was performed. Thereby a waste solution solidifying agent (18) was obtained. Thereupon, a solidification time when 1000 ml of a 0.90 mass % aqueous sodium chloride solution at 25° C. placed in a measuring cylinder of an effective volume of 1000 ml (inner diameter 66 mm) was measured. Results are shown in Table 1.

Example 19

An amount of 200 g of water-absorbent resin (D) was placed into a cooking cutter, and 4.0 g of a 92.5 mass % methanol/5 mass % methyl ethyl ketone solution in which 2.5 mass % of an alkaline water-soluble resin (M) had been dissolved was added dropwise while stirring and mixing, and this was mixed. After allowing to stand at room temperature to volatilize a solvent, this was passed through a 850 μm sieve to obtain a water-absorbent resin (N)=a waste solution solidifying agent (19).

A solidification time when 1000 ml of a 0.90 mass % aqueous sodium chloride solution at 25° C. placed in a measuring cylinder of an effective volume of 1000 ml (inner diameter 66 mm) was measured. Results are shown in Table 1.

Comparative Example 1

Using 40 g of a water-absorbent resin (A), a solidification time when 1000 ml of a 0.90 mass % aqueous sodium chloride solution at 25° C. placed in a measuring cylinder having an effective volume of 1000 ml (inner diameter 66 mm) was solidified, was measured. Results are shown in Table 1.

Comparative Example 2

The same procedure as that of Comparative Example 1 was performed except that a water-absorbent resin (A) was changed to a water-absorbent resin (B). A solidification time, and a solidifying agent floating rate when 1000 ml of a 0.90 mass % aqueous sodium chloride solution at 25° C. placed in a measuring cylinder having an effective volume of 1000 ml (inner diameter 66 mm) was solidified, were measured. Further, a concentration distribution of a waste solution solidifying agent in a measuring cylinder, and a standard deviation thereof were obtained. Results are shown in Table 1.

In addition, a 0.90 mass % aqueous sodium chloride solution containing 20 mass % of defibered cattle blood was solidified similarly, a solidification time was measured, and a concentration distribution of a waste solution solidifying agent in a measuring cylinder, and a standard deviation thereof were obtained. Results are shown in Table 2.

Comparative Example 3

According to the same manner as that of Example 2 except that an amount of zinc stearate was changed to 12.0 mass %, the same procedure was performed. A solidification time and a solidifying agent floating rate when 1000 ml of a 0.90 mass % aqueous sodium chloride solution at 25° C. placed in a measuring cylinder having an effective volume of 1000 ml (inner diameter 66 mm) was solidified were measured. Results are shown in Table 1.

In addition, a 0.90 mass % aqueous sodium chloride solution containing 20 mass % of defibered cattle blood was solidified similarly, a solidification time was measured, and a concentration distribution of a waste solution solidifying agent in a measuring cylinder, and a standard deviation thereof were obtained. Results are shown in Table 2.

Comparative Example 4

According to the same manner as that of Example 2 except that an amount of zinc stearate was changed to 0.0001 mass %, the same procedure was performed. A solidification time and a solidifying agent floating rate when 1000 ml of a 0.90 mass % aqueous sodium chloride solution at 25° C. placed in a measuring cylinder having an effective volume of 1000 ml (inner diameter 66 mm) was solidified were measured. Results are shown in Table 1.

TABLE 1

| | | | | | | | | |
|---|---|---|---|---|---|---|---|---|
| | | | | Results in 0.9 mass % aqueous sodium chloride solution | | | | |
| | Waste solution solidifying agent obtained | Water-absorbent resin | Average particle diameter (μm) | Hydrophobic substance | Hydrophilic substance | Methanol index of hydrophobic substance | Amount of solidifying agent (g) | Solidifying time (seconds) |
| Example 1 | 1 | A | 440 | Zinc stearate 0.10 mass % | | 200 or more | 40 | 420 |
| Example 2 | 2 | B | 430 | Zinc stearate 0.10 mass % | | " | " | 420 |

TABLE 1-continued

Results in 0.9 mass % aqueous sodium chloride solution

| | | | | | | | | |
|---|---|---|---|---|---|---|---|---|
| Example 3 | 3 | " | 432 | Aerosil R972 0.20 mass % | | 47 | " | 430 |
| Example 4 | 4 | " | 429 | Zinc stearate 0.20 mass % | Aerosil 200 0.20 mass % | 200 or more | " | 510 |
| Example 5 | 5 | " | 435 | FLO-THENE F-1.5 4.00 mass % | | " | " | 370 |
| Example 6 | 6 | " | 425 | Powder Base M 0.15 mass % | | " | " | 410 |
| Example 7 | 7 | " | 422 | Japanese Pharmacopoeia calcium stearate 0.15 mass % | | 170 | " | 485 |
| Example 8 | 8 | " | 435 | Erucic acid amide 0.60 mass % | | 150 | " | 480 |
| Example 9 | 9 | " | 440 | Unister M-9676 0.40 mass % | | 150 | " | 380 |
| Example 10 | 10 | D | 230 | Zinc stearate 0.10 mass % | | 200 or more | " | 430 |
| Example 11 | 11 | E | 202 | Zinc stearate 0.10 mass % | | 200 or more | " | 420 |
| Example 12 | 12 | F | 220 | Zinc stearate 0.10 mass % | | " | " | 420 |
| Example 13 | 13 | G | 400 | Zinc stearate 0.10 mass % | | " | " | 400 |
| Example 14 | 14 | H | 403 | Zinc stearate 0.10 mass % | | " | " | 420 |
| Example 15 | 15 | I | 440 | Zinc stearate 0.10 mass % | | " | " | 380 |
| Example 16 | 16 | K | 440 | Zinc stearate 0.10 mass % | | " | " | 250 |
| Example 17 | 17 | L | 445 | Zinc stearate 0.10 mass % | | " | " | 350 |
| Example 18 | 18 | B 50 mass % + L 50 mass % | 440 | Zinc stearate 0.10 mass % | | " | " | 420 |
| Example 19 | 19 | N | 420 | ASP (0.25 mass %) 4.00 mass % | | " | " | 420 |
| Comparative Example 1 | | A | 440 | | | | " | Not solidifying |
| Comparative Example 2 | | B | 430 | | | | " | 660 |
| Comparative Example 3 | | B | 430 | Zinc stearate 12.0 mass % | | 200 or more | " | Not solidifying |
| Comparative Example 4 | | B | 431 | Zinc stearate 0.0001 mass % | | " | " | Not solidifying |

| | Floating amount of solidifying agent (mass %) | Concentration distribution of water-absorbent resin (mass %) | | | | | Standard deviation | Covering index |
|---|---|---|---|---|---|---|---|---|
| | | 1000 L-800 L | 800 L-600 L | 600 L-400 L | 400 L-200 L | 200 L-0 L | | |
| Example 1 | 50.4 | 21 | 20 | 19 | 18 | 22 | 1.4 | 0.35 |
| Example 2 | 54.1 | 20 | 19 | 18 | 21 | 22 | 1.4 | 0.38 |
| Example 3 | 45.5 | 22 | 21 | 18 | 18 | 21 | 1.7 | |
| Example 4 | 52.4 | 21 | 20 | 20 | 20 | 19 | 0.6 | |
| Example 5 | 48.6 | 26 | 20 | 14 | 18 | 22 | 4.0 | |
| Example 6 | 42.9 | 22 | 19 | 19 | 20 | 20 | 1.1 | |
| Example 7 | 48.9 | 22 | 19 | 18 | 19 | 22 | 1.7 | |
| Example 8 | 48.9 | 20 | 18 | 19 | 20 | 23 | 1.7 | |
| Example 9 | 46.7 | 21 | 20 | 19 | 18 | 22 | 1.4 | |
| Example 10 | 49.9 | 25 | 20 | 16 | 16 | 23 | 3.6 | |
| Example 11 | 54.0 | 25 | 19 | 15 | 18 | 23 | 3.6 | |
| Example 12 | 54.0 | 25 | 19 | 15 | 18 | 23 | 3.6 | |
| Example 13 | 39.0 | 25 | 20 | 16 | 16 | 23 | 3.6 | |
| Example 14 | 51.3 | 18 | 17 | 18 | 21 | 26 | 3.3 | |
| Example 15 | 40.0 | 18 | 17 | 18 | 21 | 26 | 3.3 | |
| Example 16 | 62.4 | 29 | 18 | 16 | 18 | 19 | 4.6 | |
| Example 17 | 65.0 | 29 | 21 | 18 | 17 | 15 | 4.9 | |
| Example 18 | 54.0 | 18 | 17 | 18 | 21 | 26 | 3.3 | |
| Example 19 | 60.0 | 22 | 20 | 18 | 18 | 22 | 1.8 | |
| Comparative Example 1 | 0.5 | 8 | 10 | 15 | 25 | 42 | 12.5 | 0.00 |

TABLE 1-continued

| | | Results in 0.9 mass % aqueous sodium chloride solution | | | | | | | |
|---|---|---|---|---|---|---|---|---|---|
| Comparative Example 2 | 1.0 | 14 | 16 | 16 | 22 | 32 | 6.6 | 0.00 |
| Comparative Example 3 | 98.0 | 45 | 25 | 13 | 10 | 7 | 13.9 | 0.95 |
| Comparative Example 4 | 0.0 | 7 | 13 | 15 | 25 | 40 | 11.6 | 0.05 |

Note)
As to particle size of water-absorbent resin, a portion larger than 850 μm was 0 mass %, and a portion smaller than 100 μm was less than 1.5 mass %.

TABLE 2

Results in 0.9 mass % aqueous sodium chloride solution containing 20 mass % of defibered cattle blood

| | Water-absorbent resin obtained | Methanol index of Hydrophobic substance | Amount of solidifying hydrophobic substance | Solidifying agent (g) | Solidifying time (min) | Concentration distribution of water-absorbent resin (mass %) | | | | | Standard deviation |
|---|---|---|---|---|---|---|---|---|---|---|---|
| | | | | | | 3000 L-2400 L | 2400 L-1600 L | 1600 L-1200 L | 1200 L-600 L | 600 L-0 L | |
| Example 1 | A | Zinc stearate 0.10 mass % | 200 or more | 99 | 24 | 25 | 20 | 15 | 18 | 22 | 3.4 |
| Example 2 | B | Zinc stearate 0.10 mass % | " | " | 25 | 22 | 20 | 18 | 18 | 22 | 1.8 |
| Example 14 | H | Zinc stearate 0.10 mass % | " | " | 20 | 25 | 18 | 17 | 18 | 22 | 3.0 |
| Example 15 | I | Zinc stearate 0.10 mass % | " | " | 24 | 23 | 21 | 17 | 18 | 21 | 2.2 |
| Example 16 | K | Zinc stearate 0.10 mass % | " | " | 22 | 26 | 23 | 14 | 16 | 21 | 4.4 |
| Comparative Example 2 | B | | | " | Not solidifying | 10 | 10 | 15 | 25 | 40 | 11.4 |
| Comparative Example 3 | B | Zinc stearate 12.0 mass % | 200 or more | " | Not solidifying | 50 | 20 | 13 | 9 | 8 | 16.3 |

Regarding waste solution solidifying agents obtained in Examples 1 to 17 and Comparative Examples 1 to 4, a moisture absorption flowability index before impartation of an impact force, a moisture absorption flowability index after impartation of an impact force, a moisture absorption flowability retention index, absorption capacity under load (AAP) before impartation of impact force, absorption capacity under load (AAP) after impartation of an impact force, absorption capacity under load (AAP) retention index, water absorption capacity (CRC) and a bulk density are shown in Table 3.

TABLE 3

| | Waste solution solidifying agent obtained | Water-absorbent resin | Moisture absorption flowability index before giving impact | Moisture absorption flowability index after giving impact | Moisture absorption flowability retaining index | AAP 2.06 kPa (before impact) (g/g) | AAP 4.83 kPa (before impact) (g/g) |
|---|---|---|---|---|---|---|---|
| Example 1 | 1 | A | 100.0 | 100.0 | 1.00 | 11 | 9 |
| Example 2 | 2 | B | 100.0 | 100.0 | 1.00 | 31 | 25 |
| Example 3 | 3 | " | 100.0 | 100.0 | 1.00 | 32 | 26 |
| Example 4 | 4 | " | 100.0 | 100.0 | 1.00 | 32 | 25 |
| Example 5 | 5 | " | 93.0 | 92.0 | 0.99 | 31 | 26 |
| Example 6 | 6 | " | 99.3 | 100.0 | 1.01 | 32 | 24 |
| Example 7 | 7 | " | 100.0 | 100.0 | 1.00 | 32 | 25 |
| Example 8 | 8 | " | 100.0 | 100.0 | 1.00 | 32 | 24 |
| Example 9 | 9 | " | 99.9 | 99.9 | 1.00 | 32 | 26 |
| Example 10 | 10 | D | 100.0 | 100.0 | 1.00 | 35 | 26 |
| Example 11 | 11 | E | 100.0 | 100.0 | 1.00 | 10 | 9 |
| Example 12 | 12 | F | 98.0 | 95.0 | 0.97 | 18 | 17 |
| Example 13 | 13 | G | 98.0 | 95.0 | 0.98 | 10 | 9 |
| Example 14 | 14 | H | 100.0 | 100.0 | 1.00 | 18 | 17 |
| Example 15 | 15 | I | 95.0 | 91.0 | 0.96 | 30 | 24 |
| Example 16 | 16 | K | 95.0 | 94.0 | 0.99 | 8 | 6 |
| Example 17 | 17 | L | 95.0 | 92.0 | 0.97 | 31 | 24 |
| Example 18 | 18 | B 50 mass % + L 50 mass % | 98.0 | 85.0 | 0.87 | 29 | 24 |

TABLE 3-continued

| | | | | | | | |
|---|---|---|---|---|---|---|---|
| Example 19 | 19 | N | 98.0 | 98.0 | 1.00 | 32 | 26 |
| Comparative Example 1 | | A | 16.3 | 3.0 | 0.18 | 11 | 9 |
| Comparative Example 2 | | B | 46.3 | 10.6 | 0.23 | 30 | 26 |
| Comparative Example 3 | | B | 100 | 100.0 | 1.00 | 31 | 26 |
| Comparative Example 4 | | B | 15 | 5.0 | 0.33 | 30 | 25 |

| | AAP 2.06 kPa (after impact) (g/g) | AAP 4.83 kPa (after impact) (g/g) | AAP retaining index 2.06 kPa | AAP retaining index 4.83 kPa | CRC (g/g) | Bulk density (g/cm³) |
|---|---|---|---|---|---|---|
| Example 1 | 10 | 9 | 0.91 | 1.00 | 38.7 | 0.71 |
| Example 2 | 30 | 24 | 0.97 | 0.96 | 31.2 | 0.72 |
| Example 3 | 31 | 25 | 0.97 | 0.96 | 32.0 | 0.70 |
| Example 4 | 30 | 26 | 0.94 | 1.04 | 31.2 | 0.71 |
| Example 5 | 30 | 25 | 0.97 | 0.96 | 31.3 | 0.72 |
| Example 6 | 31 | 22 | 0.97 | 0.92 | 31.0 | 0.71 |
| Example 7 | 31 | 24 | 0.97 | 0.96 | 31.9 | 0.71 |
| Example 8 | 31 | 23 | 0.97 | 0.96 | 31.8 | 0.70 |
| Example 9 | 31 | 25 | 0.97 | 0.96 | 32.1 | 0.71 |
| Example 10 | 34 | 25 | 0.97 | 0.96 | 35.0 | 0.70 |
| Example 11 | 9 | 8 | 0.90 | 0.89 | 35.0 | 0.95 |
| Example 12 | 15 | 14 | 0.83 | 0.82 | 30.0 | 0.96 |
| Example 13 | 9 | 8 | 0.97 | 0.97 | 30.0 | 0.65 |
| Example 14 | 15 | 14 | 0.97 | 0.97 | 30.0 | 0.65 |
| Example 15 | 28 | 22 | 0.93 | 0.92 | 29.0 | 0.65 |
| Example 16 | 7 | 5 | 0.88 | 0.83 | 30.0 | 0.45 |
| Example 17 | 29 | 21 | 0.94 | 0.88 | 28.7 | 0.45 |
| Example 18 | 27 | 21 | 0.93 | 0.88 | 29.0 | 0.58 |
| Example 19 | 31 | 25 | 0.97 | 0.96 | 31.3 | 0.71 |
| Comparative Example 1 | 8 | 6 | 0.73 | 0.67 | 38.2 | 0.66 |
| Comparative Example 2 | 25 | 22 | 0.83 | 0.85 | 30.3 | 0.67 |
| Comparative Example 3 | 31 | 26 | 1.00 | 1.00 | 22.4 | 0.66 |
| Comparative Example 4 | 20 | 15 | 0.67 | 0.75 | 32.0 | 0.69 |

INDUSTRIAL APPLICATION

As described above, the waste solution solidifying agent of the present invention is obtained from a water-absorbent resin particle and a substance having a certain particular hydrophobicity.

When a waste solution containing blood, body fluid or the like is solidified using the particulate waste solution solidifying agent of the present invention, at least a part of a waste solution solidifying agent is floated, thereby, solidification progresses from an upper part and a lower part of a waste solution, therefore, in particular, when a vertically oriented canister is used, a time until solidification of a whole waste solution can be remarkably shortened. In addition, since a part of a floating waste solution solidifying agent is settled, in other words, the agent is settled while absorbing a liquid, the effect of further shortening a time until solidification of a whole waste solution is also exerted.

Therefore, the waste solution solidifying agent of the present invention can be effectively utilized for solidifying various waste solutions such as beverage waste solution, factory waste solution, radiation waste solution, and excretion waste solution, particularly, a waste solution containing blood or body fluid.

The invention claimed is:

1. A method of solidifying a medical waste solution, which is a method of treating a medical waste solution containing blood or body fluid comprising placing a treating agent into a medical waste solution containing blood or body fluid in an effective amount to solidify the medical waste solution into a gel, wherein the treating agent is a particulate waste solution solidifying agent, said waste solution solidifying agent comprising, as an essential component, a water-absorbent resin having a crosslinked structure obtained by polymerizing a monomer containing acrylic acid and/or a salt thereof as a main component, and further comprising a non-volatile hydrophobic substance powder having a methanol index of 20 or more, wherein when placed in a 0.90 mass % aqueous sodium chloride solution at once, 20 to 95 mass % of the agent is floated, and 80 to 5 mass % of the agent is settled, provided that floating and settling are defined by the state at one minute after placement of 40 g of a particulate waste solution solidifying agent at once in a measuring cylinder having an effective volume of 1000 ml (inner diameter 66 mm) which has a vertical axial direction and contains 1000 ml of a 0.90 mass % aqueous sodium chloride solution at 25° C., and the hydrophobic substance being a powder where 90 to 100 mass % of the powder has a particle diameter of 200 μm or smaller, and the amount of the hydrophobic substance powder is 0.001 to 10 mass % relative to the total amount of the water-absorbent resin particles, and wherein Methanol Index: when 1 g of a hydrophobic substance is added to 50 ml of pure water at 25° C., in the case where the hydrophobic substance is a solid, a volume (ml) of methanol at 25° C. necessary for wetting, or in the case where the hydrophobic substance is a liquid, a volume (ml) of methanol at 25° C. necessary for dispersing and/or emulsifying the hydrophobic substance.

2. The method of solidifying a medical waste solution according to claim 1, wherein when the waste solution solidifying agent is placed into a 0.90 mass % aqueous sodium chloride solution at once, 25 to 80 mass % of the agent is floated, and 75 to 20 mass % of the agent is settled.

3. The method of solidifying a medical waste solution according to claim 1, wherein when 40 g of a waste solution solidifying agent is placed at once in a measuring cylinder of an effective volume 1000 ml (inner diameter 66 mm) which stands with a vertical axial direction and contains 1000 ml of a 0.90 mass % aqueous sodium chloride solution at 25° C., a solidification time of from the placement to solidification of the aqueous sodium chloride solution is 60 to 700 seconds.

4. The method of solidifying a medical waste solution according to claim 1, wherein when 99 g of a waste solution solidifying agent is placed at once in a measuring cylinder of an effective volume 3000 ml (inner diameter 103 mm) which stands with a vertical axial direction and contains 3000 ml of an aqueous solution at 25° C. containing 20 mass % of defibered cattle blood relative to a 0.90 mass % aqueous sodium chloride solution, a solidification time of from the placement to solidification of the aqueous solution is 5 to 50 minutes.

5. The method of solidifying a medical waste solution according to claim 1, wherein when 40 g of a waste solution solidifying agent is placed at once in a measuring cylinder of an effective volume 1000 ml (inner diameter 66 mm) which stands with a vertical axial direction and contains 1000 ml of a 0.90 mass % aqueous sodium chloride solution at 25° C., a distribution of a water-absorbent resin after completion of solidification of the aqueous solution is 0 to 6 as expressed by a standard deviation.

6. The method of solidifying a medical waste solution according to claim 1, wherein when 99 g of a waste solution solidifying agent is placed at once in a measuring cylinder of an effective volume 3000 ml (inner diameter 103 mm) which stands with a vertical axial direction and contains 3000 ml of an aqueous solution at 25° C. containing 20 mass % of defibered cattle blood relative to a 0.90 mass % aqueous sodium chloride solution, a distribution of a water-absorbent resin after completion of solidification of the aqueous solution is 0 to 6 as expressed by a standard deviation.

7. The method of solidifying a medical waste solution according to claim 1, wherein the surface of the water-absorbent resin is further crosslinking-treated.

8. The method of solidifying a medical waste solution according to claim 1, said treating agent further comprising a hydrophilic substance having a methanol index of 0 to less than 20, in addition to the water-absorbent resin and a hydrophobic substance.

9. The method of solidifying a medical waste solution according to claim 1, wherein the hydrophobic substance is a solid at a normal temperature (25° C.) and a normal pressure.

10. The method of solidifying a medical waste solution according to claim 1, wherein the water-absorbent resin is granulated.

11. The method of solidifying a medical waste solution according to claim 1, wherein the waste solution solidifying agent with the hydrophobic substance added thereto has a covering index of a hydrophobic substance in a range of not less than 0.10 to less than 0.80.

12. The method of solidifying a medical waste solution according to claim 1, wherein the water-absorbent resin is an irregularly pulverized shape substance.

13. The method of solidifying a medical waste solution according to claim 1, wherein said hydrophobic substance is selected from the group consisting of a hydrocarbon, fatty acid, fatty acid ester, fatty acid amide, metal soap, silicone-based compound, surfactant and thermoplastic resin.

14. The method of solidifying a medical waste solution according to claim 1, wherein the content of the water-absorbing resin in the waste solution solidifying agent is 50 to 100 mass %.

15. The method of solidifying a medical waste solution according to claim 1, wherein the bulk density of the waste solution solidifying agent is 0.30 to 0.90 g/cm$^3$, and the true density of the waste solution solidifying agent is 1.1 to 2.0 g/cm$^3$.

16. The method of solidifying a medical waste solution according to claim 1, wherein the hydrophobic substance powder has a particle diameter smaller than a weight average particle diameter of said water-absorbent resin.

17. The method of solidifying a medical waste solution according to claim 1, wherein the hydrophobic substance powder is immobilized on a surface of the water-absorbent resin.

18. The method of solidifying a medical waste solution of claim 1, wherein said waste solution solidifying agent is added to the medical waste solution so that solidification progresses from an upper part of the waste solution to a lower part of the waste solution as part of the waste solution solidifying agent settles from the upper part to the lower part, and where a remainder of the waste solution solidifying agent floats on the waste solution.

19. The method of solidifying a medical waste solution of claim 18, wherein said waste solution is contained in a vertically oriented canister, and said method comprises adding said waste solution solidifying agent to said waste solution in said canister.

20. The method of solidifying a medical waste solution of claim 1, wherein said medical waste solution is blood.

21. The method of solidifying a medical waste solution of claim 1, wherein said medical waste solution is body fluid containing blood.

22. The method of solidifying a medical waste solution of claim 1, further comprising
adding the waste solution solidifying agent to the medical waste solution to form a mixture and solidifying the resulting mixture.

* * * * *